(12) United States Patent
Bilgicer et al.

(10) Patent No.: US 9,872,870 B2
(45) Date of Patent: Jan. 23, 2018

(54) MULTIFUNCTIONAL MICELLAR NANOPARTICLE-BASED DRUG AND TARGETING AGENT SYSTEM

(71) Applicant: University of Notre Dame du Lac, Notre Dame, IN (US)

(72) Inventors: Zihni Basar Bilgicer, Granger, IN (US); Tanyel Kiziltepe Bilgicer, Granger, IN (US); Jonathan Darryl Ashley, Olathe, KS (US); Jared Stefanick, Mishawaka, IN (US); Nathan J. Alves, Woodbury, CT (US); Michael W. Handlogten, Rochester, MN (US)

(73) Assignee: University of Notre Dame du Lac, Notre Dame, IN (US)

( * ) Notice: Subject to any disclaimer, the term of this patent is extended or adjusted under 35 U.S.C. 154(b) by 43 days.

(21) Appl. No.: 14/356,121

(22) PCT Filed: Nov. 5, 2012

(86) PCT No.: PCT/US2012/063614
§ 371 (c)(1),
(2) Date: May 2, 2014

(87) PCT Pub. No.: WO2013/067537
PCT Pub. Date: May 10, 2013

(65) Prior Publication Data
US 2014/0287049 A1    Sep. 25, 2014

Related U.S. Application Data

(60) Provisional application No. 61/628,741, filed on Nov. 4, 2011.

(51) Int. Cl.
A61K 9/133  (2006.01)
A61K 38/08  (2006.01)
(Continued)

(52) U.S. Cl.
CPC .......... *A61K 31/704* (2013.01); *A61K 31/351* (2013.01); *A61K 47/62* (2017.08);
(Continued)

(58) Field of Classification Search
None
See application file for complete search history.

(56) References Cited

U.S. PATENT DOCUMENTS 5,534,499 A * 7/1996 Ansell .................. A61K 9/1271
424/1.21
2003/0082103 A1* 5/2003 Wartchow .......... A61K 49/0002
424/1.53
(Continued)

FOREIGN PATENT DOCUMENTS

WO    WO 96/06108    *  2/1996  .............. C07K 5/10
WO    2009-031859 A2    3/2009

OTHER PUBLICATIONS

Hruby, M. et al. J. Controlled Rel. (2005), pp. 137-148.*
(Continued)

*Primary Examiner* — Kevin S Orwig
(74) *Attorney, Agent, or Firm* — Haukaas Fortius PLLC; Michael H. Haukaas

(57) ABSTRACT

Embodiments provide systems, methods, and compositions for nanoparticle-based drug delivery to target cells or tissues. A drug delivery system may include a nanoparticle with a targeting component and a therapeutic component. The nanoparticle may have a predetermined number or valence of targeting molecules for multivalent interaction with a target cell or tissue. Binding of the targeting molecules to the target cell may result in receptor-mediated uptake of the nanoparticle by the target cell. The therapeutic component may be subsequently released within an endocytic vesicle of the target cell. Nanoparticle-based drug delivery systems as described herein may provide improved efficacy and/or reduced toxicity.

18 Claims, 11 Drawing Sheets

(51) Int. Cl.

| | | |
|---|---|---|
| *A61K 31/704* | (2006.01) | |
| *A61K 51/04* | (2006.01) | |
| *A61K 31/351* | (2006.01) | |
| *A61K 47/62* | (2017.01) | |
| *A61K 47/69* | (2017.01) | |
| *A61K 9/107* | (2006.01) | |

(52) U.S. Cl.
CPC ...... *A61K 47/6907* (2017.08); *A61K 47/6909* (2017.08); *A61K 51/0455* (2013.01); *A61K 9/1075* (2013.01)

(56) References Cited

U.S. PATENT DOCUMENTS

| | | |
|---|---|---|
| 2011/0104258 A1 | 5/2011 | Pit et al. |
| 2011/0244048 A1 | 10/2011 | Amiji et al. |
| 2012/0135064 A1* | 5/2012 | Campbell .............. C07K 16/22 424/450 |

OTHER PUBLICATIONS

Sanz-Rodriguez, F., et al. Leuk. Lymphoma (2001), 41, pp. 239-245.*
Damiano, J., et al. Blood (1999), 93; pp. 1658-1667.*
Noborio-Hatano, K., et al. Oncogene (Oct. 2008), 28; pp. 231-242.*
Olson, D. L., et al. Mol. Cancer Ther. (2005), 4; pp. 91-99.*
Jackson, D. Y., et al. J. Med. Chem. (1997), 40; pp. 3359-3368.*
Ogier, J. et al., "Recent Advances in the Field of Nanometric Drug Carriers," Future Medicinal Chemistry, 2009, vol. 1, No. 4, pp. 693-711.
Ganta, S. et al., "A Review of Stimuli-responsive Nanocarriers for Drug and Gene Delivery," Journal of Controlled Release, 2008, vol. 126, pp. 187-204.
Kiziltepe, T. et al., "Rationally Engineered Nanoparticles Target Multiple Myeloma Cells, Overcome Cell-adhesion-mediated Drug Resistance, and Show Enhanced Efficacy in vivo," Blood Cancer Journal, Apr. 20, 2012 (e-pub), vol. 2, Article No. e64.

* cited by examiner

1400

1401
Select a target cell or tissue for treatment with a first therapeutic agent, wherein the surface of the selected target cell or tissue includes a first surface receptor

1403
Select a ligand that binds to the first surface receptor

1405
Couple the ligand to a first lipid to form a first component

1407
Couple the first therapeutic agent to a second lipid to form a second component

1409
Add quantities of the first component, the second component, and a third component to a first solvent in a predetermined molar ratio to form nanoparticles, wherein the third component comprises polyethylene glycol (PEG)

1411
Administer the nanoparticles to a patient in need thereof

1413
Measure the effect of the nanoparticles on the target cell or tissue

FIGURE 14

MULTIFUNCTIONAL MICELLAR NANOPARTICLE-BASED DRUG AND TARGETING AGENT SYSTEM

CROSS REFERENCE TO RELATED APPLICATIONS

The present application claims the benefit of U.S. Patent Application No. 61/628,741, filed Nov. 4, 2011, entitled "Engineering Multifunctional Nanoparticles to Overcome Cell Adhesion Mediated Drug Resistance and Inhibit Tumor Growth in Multiple Myeloma," the entire disclosure of which is hereby incorporated by reference in its entirety.

TECHNICAL FIELD

Embodiments herein relate to the field of drug delivery, and, more specifically, to nanoparticle-based drug delivery systems and methods.

SEQUENCE LISTING

The present application includes a Sequence Listing in electronic format as a text file titled "Seq_Listing.txt" which was created on Nov. 5, 2012 and has a size of 2,241 bytes. The contents of txt file "Seq_Listing.txt" are incorporated by reference herein.

BACKGROUND

Multiple myeloma (MM) is a B-cell malignancy characterized by proliferation of monoclonal plasma cells in the bone marrow (BM). Despite recent advances in treatment strategies and the emergence of novel therapies, it remains incurable (median survival of 4-5 years) due to the development of drug resistance. A major factor that leads to drug resistance in MM patients is the adhesion of MM cells to the BM stroma. This results in cell-adhesion-mediated drug resistance (CAM-DR), which renders the MM cells in the BM microenvironment less sensitive to chemotherapeutic agents.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 14 illustrates a flow diagram of a method for designing and using a drug delivery nanoparticle to treat a target cell or tissue, all in accordance with various embodiments.

DETAILED DESCRIPTION OF DISCLOSED EMBODIMENTS

Figure 1:
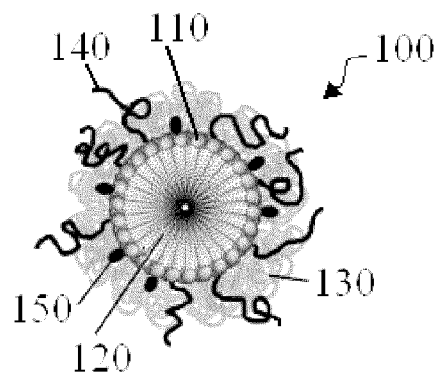
FIG. 1 illustrates an embodiment of a drug delivery nanoparticle.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, methods, apparatuses, and systems for targeted drug delivery are provided. In exemplary embodiments, a computing system may be employed to perform, or to control devices employed to perform, one or more methods as disclosed herein.

Embodiments described herein provide nanoparticle-based drug delivery systems and methods. In some embodiments, a drug delivery system may include a nanoparticle with a targeting component and a therapeutic component. The nanoparticle may have a predetermined number or valence of targeting molecules for multivalent interaction with a target cell or tissue. Binding of the targeting molecules to the target cell may result in receptor-mediated uptake of the nanoparticle by the target cell. The therapeutic component may be subsequently released within an endocytic vesicle of the target cell.

As used herein, a "targeting molecule" or "targeting agent" is a peptide, cyclic peptide, peptidomimetic, or other molecule that binds to a targeted molecule (e.g., a cell surface molecule of a cell targeted for treatment, and/or an extracellular matrix component). Optionally, the binding affinity of the targeting molecule may be in the range of 1 nM to 1 µM. In some embodiments, the targeting molecule may be an antagonist of a receptor on the surface of a targeted cell.

As used herein, a "therapeutic agent" can be any type of molecule used in the treatment, cure, prevention, or diagnosis of a disease or other medical condition. Examples of therapeutic agents include, but are not limited to, drugs (e.g., anti-cancer drugs, antibiotics) and nucleic acids (e.g., siRNA, DNA). Specific examples of therapeutic agents include, but are not limited to, bortezomib, carfilzomib, and platinum-containing drugs (e.g., cisplatin, carboplatin, derivatives thereof).

FIG. 1 illustrates an embodiment of a drug delivery nanoparticle 100, in accordance with various embodiments. A nanoparticle 100 may be designed for use to prevent, treat, or cure a disease or other medical condition. As illustrated, nanoparticle 100 may have a hydrophobic interior portion 120 surrounded by an outer portion that includes polar head groups 110, water-soluble polymers 130, targeting molecules 140, and therapeutic agent molecules 150. Nanoparticle 100 may include at least three groups of component molecules, which are shown in FIG. 1b as components 102, 104, and 106. As used herein, the term "component" may refer to one molecule of a particular species (e.g., one molecule of component 102) or to a plurality of molecules of a particular species (e.g., two or more molecules of component 102).

Nanoparticle 100 may include components 102, 104, and/or 106 in a predetermined ratio. As used herein, a "molecular ratio" may be provided to indicate the number of molecules of two or more components (e.g., 102, 104, 106) in a nanoparticle. The number of molecules of a component in a nanoparticle may also be described in terms of a "mole percentage," which is calculated by dividing the number of molecules of that component by the number of molecules in the nanoparticle. For example, in a nanoparticle with about 90 component molecules, 60 of which are component 102, 20 of which are component 114, and 10 of which are component 116, the "molecular ratio" of the components (112:114:116) is 60:20:10, and the mole percentages of the three components are 67%, 22%, and 11%, respectively.

Figure 2A:
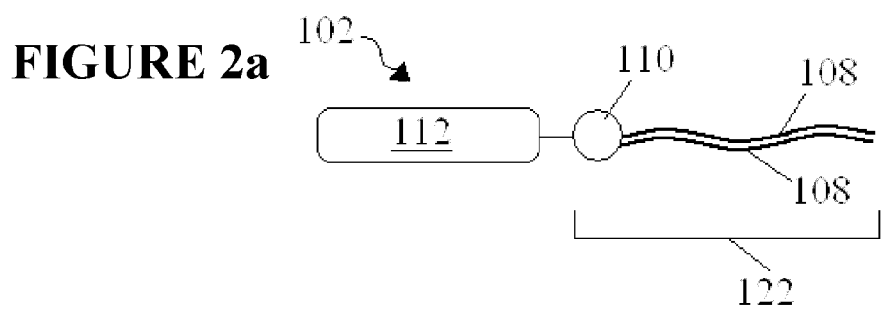
FIGS. 2a-2c illustrate components of the drug delivery nanoparticle of FIG. 1.
Figure 2B:
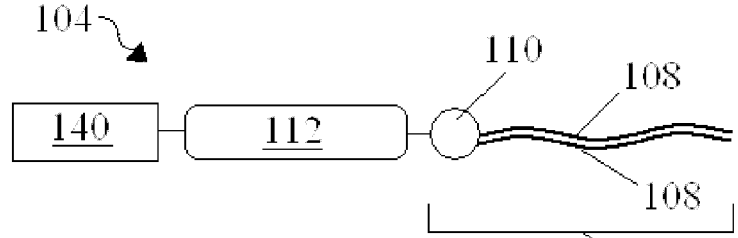
Figure 2C:
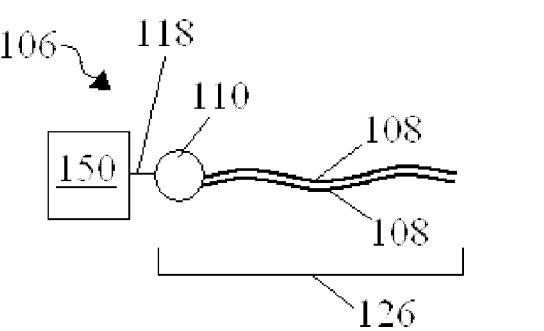

FIGS. 2a-2c are schematic diagrams of components 102 (FIG. 2a), 104 (FIG. 2b), and 106 (FIG. 2c). Components 102, 104, and 106 may each include a lipid molecule (122, 124, and 126, respectively) coupled directly or indirectly to one or more additional molecules. Typically, lipid molecules 122, 124, and 126 are amphipathic lipid molecules, each with a polar/hydrophilic portion 110 and a non-polar/hydrophobic portion 108. Optionally, some or all of the lipid molecules may be phospholipids. In some examples, lipid molecules 122, 124, and/or 126 may be different chemical species. Alternatively, two or more of lipid molecules 122, 124, and 126 may be the same chemical species. For example, lipid molecule 122 and lipid molecule 124 may be the same chemical species (e.g., DSPE) and lipid molecule 126 may be a different chemical species (e.g., DPPE-GA).

Referring now to FIG. 2a, component 102 may be configured to enhance the stability and/or circulation time of nanoparticle 100. In some embodiments, component 102 may include a polymer 112 conjugated or otherwise coupled to lipid molecule 122. Polymer 112 may be a water-soluble polymer, such as polyethylene glycol (PEG). In other embodiments, polymers 112 may be polymeric sugars, PLGA, and/or other biocompatible water soluble molecules. In one embodiment, component 102 may be a lipid-PEG block copolymer (e.g., DSPE-PEG2000).

As shown in FIG. 2b, component 104 may be configured to target nanoparticle 100 to a particular cell or tissue type. In some embodiments, component 104 may include a targeting molecule 140 and a polymer 112 conjugated or otherwise coupled to lipid molecule 124. For example, targeting molecule 140 may be coupled to a first end of polymer 112, and lipid molecule 124 may be coupled to an opposite second end of polymer 112.

Targeting molecule 140 may be, or may include, a peptide, a cyclic peptide, a peptidomimetic, and/or a small molecule. Targeting molecule 140 may be configured to bind to a component of extracellular matrix (ECM) and/or to a cell surface molecule of a target cell. Examples of such cell surface molecules include, but are not limited to, integrins, cadherins, selectins, and syndecans. In some embodiments, the cell surface molecule of the target cell may be a receptor, and targeting molecule 140 may be a ligand for the receptor. In some embodiments, targeting molecule 140 may be an antagonist of the receptor. For example, targeting molecule 140 may be an antagonist that interferes with a function of the target cell (e.g., adhesion) upon binding to the receptor. Alternatively, targeting molecule 140 may be an agonist or partial agonist of the receptor.

In some examples, the cell surface molecule of the target cell/tissue may be a molecule that is expressed only by the target cells/tissue(s). In other examples, the cell surface molecule of the target cell/tissue may be a molecule that is expressed by both target cells and non-target cells, but is present in fewer numbers and/or in a different spatial arrangement on non-target cells than on target cells.

In some embodiments, binding of the targeting molecule 140 to the cell surface molecule of the target cell may trigger endocytosis of nanoparticle 100 by the target cell. Optionally, the cell surface molecule may play a role in the adhesion of the target cell to ECM and/or the surrounding environment, and binding of the targeting molecule 140 to the target cell may reduce or disrupt this adhesion.

Targeting molecule 140 may be an antagonist of a target cell surface receptor. In some embodiments, targeting molecule 140 may be a VLA-4 antagonist. In the specific example described further below, targeting molecule 140 is a VLA-4 antagonist peptide ("VLA-4-pep", YCDPC; SEQ ID NO: 1) that is configured to bind to fibronectin and to VLA-4. The structure of VLA-4-pep is shown in FIG. 3. Other examples of VLA-4 antagonists that could be used as targeting molecules include, but are not limited to, the peptide sequence CFLDFP (SEQ ID NO: 2), peptide sequences with a consensus LDV sequence, cyclic peptides with an RCD motif, sequences based on (X)CDPC (SEQ ID NO: 3), XC(Z)PC (SEQ ID NO: 4), XCA(Z)C (SEQ ID NO: 5), (X)CSPC (SEQ ID NO: 6), YC(X)C (SEQ ID NO: 7), or RC(X)PC (SEQ ID NO: 8) core structures (where X and Z are variable amino acids), peptides derived from fibronectin CS-1, peptides derived from fibronectin RGD tripeptide, peptides derived from fibronectin RGD and vascular cell adhesion molecule-1, peptides derived from anti-$\alpha_4$ monoclonal antibody, and other VLA-4 antagonists known in the art. Additional examples of VLA-4 antagonists are described in the following references: Jackson, David Y. et al., "Potent a4b1 Peptide Antagonists as Potential Anti-Inflammatory Agents," J. Med. Chem., vol. 40, pp. 3359-3368, 1997; Lin, Ko-Chung and Castro, Alfredo C., "Very late antigen 4 (VLA4) antagonists as anti-inflammatory agents," Current Opinion in Chemical Biology, vol. 2, pp. 453-457, 1998; and Tilley, Jefferson W., "Very late antigen-4 integrin antagonists," Expert Opin. Ther. Patents, vol. 18, no. 8, pp. 841-859, 2008, all of which are hereby incorporated by reference herein Alternatively, targeting molecules 140 may be antagonists and/or ligands of other receptors. Examples of other targeting molecules include, but are not limited to, folate (binds folate receptor), RGD peptide sequences against the $\alpha v \beta 3$ integrin, and peptide antagonists of the Human Epidermal Growth Factor Receptor 2 (HER2). In some embodiments, the binding affinity of targeting molecule 140 to the target cell surface receptor is in the range of 1 nM to 1 μM. Binding affinities in this range may allow for binding enhancements due to multivalent interactions.

Referring now to FIG. 2c, component 106 may include a therapeutic agent 150 coupled to lipid molecule 126. Optionally, therapeutic agent 150 may be coupled to lipid molecule 126 by a pH-sensitive bond 118. In some embodiments, pH-sensitive bond 118 may be acid-labile. For example, pH-sensitive bond 118 may be a hydrazone (HN—NH) bond.

Therapeutic agent 150 can be or can include any type of drug for which delivery to a target cell or tissue is desired. In one example, therapeutic agent 150 is doxorubicin. However, in other examples therapeutic agent 150 may be another drug, a nucleic acid (e.g., siRNA, DNA, etc.), or some combination thereof. In some embodiments, therapeutic agent 150 may be an antibiotic or an anti-cancer drug. Antibiotics and anti-cancer drugs are known in the art. Examples of suitable therapeutic agents 150 may include, but are not limited to, bortezomib, carfilzomib, and platinum-containing drugs (e.g., cisplatin, carboplatin, or a derivative thereof). Optionally, a nanoparticle may include two or more different therapeutic agents 150 coupled to the same lipid molecule or to different lipid molecules.

Nanoparticles 100 may be constructed to include components 112, 114, and 116 in predetermined molecular ratios. Stated in another way, nanoparticles 100 may be constructed using methods described herein to result in predetermined molar percentages of components 112, 114, and 116 in most or all of the nanoparticles. The molar/molecular ratios of components 102, 104, and 106 in nanoparticle 100 may vary among embodiments. In some examples, the molar percentage of component 102 may be 60-100% (e.g., 60-70%, 60-90%, 70-90%, 75-95%, 80-90%, 80-95%, or 90-100%). In other examples, the molar percentage of component 104 may be 0-60% (e.g., 0-5%, 0-40%, 1-40%, 10-30%, 15-35%, 20-30%, 20-40%, or 30-40%). In still other examples, the molar percentage of component 106 may be 0-25% (e.g., 0-5%, 1-10%, 0-20% 1-20%, 5-15%, 5-20%, or 10-20%). In a specific embodiment, component 102 may be a pegylated phospholipid (e.g., DSPE-PEG2000), and may be present in nanoparticle 100 at a molar percentage of 60% or greater in order to maintain a low CMC. Optionally, the molar percentage of component 112 may be greater than the molar percentage of component 114, which may be greater than the molar percentage of component 116. Alternatively, the molar percentage of component 116 may be greater than the molar percentage of component 114.

In a particular embodiment, component 112 is a pegylated phospholipid (e.g., DSPE-PEG2000), component 114 is a peptide-PEG-phospholipid conjugate (e.g., VLA-4-pep/DSPE-PEG2000), and component 116 is an anti-cancer drug conjugated to a phospholipid (e.g., Dox/DPPE-GA). In this embodiment, nanoparticles may include 80-100 component molecules, or about 90 component molecules. The molar percentages of components 112, 114, and 116 may be about 67%, about 22%, and about 11%, respectively. For example, nanoparticles may have about 90 component molecules, with a predetermined ratio of component 102:component 104:component 106 of about 60:20:10.

Figure 3A:
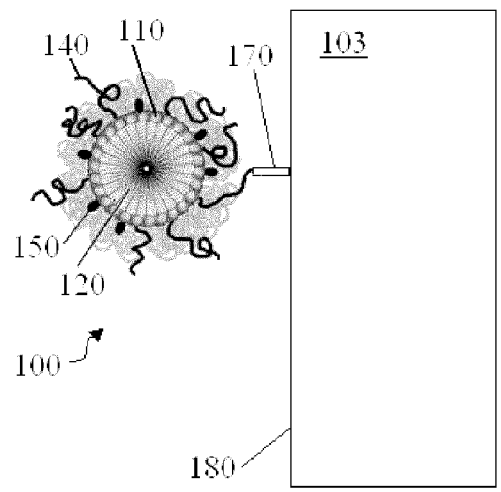
FIGS. 3a-3c are schematic diagrams of drug delivery nanoparticle uptake and drug release in a target cell.
Figure 3B:
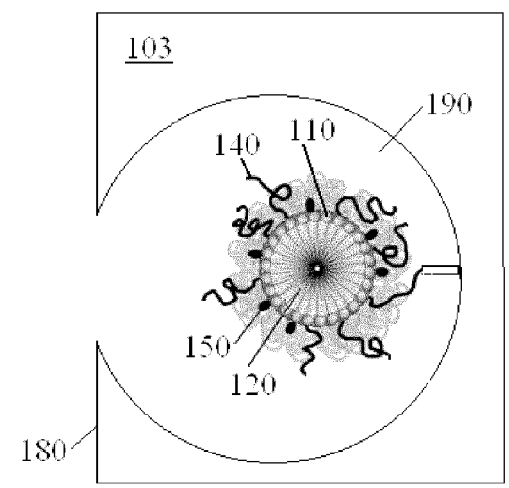
Figure 3C:
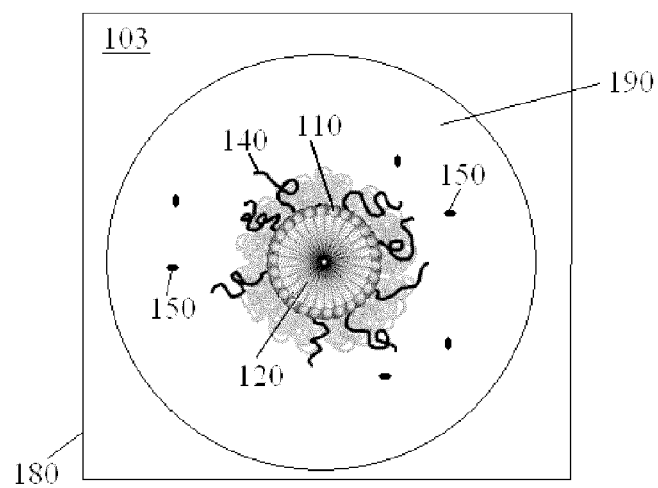

FIGS. 3a-3c are schematic diagrams of drug delivery nanoparticle uptake and drug release in a target cell, in accordance with various embodiments. FIG. 3a shows nanoparticle 100 binding to a receptor 170 on a target cell 103 via targeting molecule 140. While only a single binding event is illustrated, it is to be understood that multiple targeting molecules 140 may bind to corresponding receptors 170 on the target cell. As illustrated in FIG. 3b, the binding of targeting molecule(s) 140 to receptor(s) 170 may cause receptor-mediated uptake of nanoparticle 100 by target cell 103. Thus, nanoparticle 100 may be internalized within a vesicle 190 (e.g., an endosome/lysosome). Nanoparticle 100 may release therapeutic agent 150 within vesicle 190. The release of therapeutic agent 150 may be triggered, for example, by a reduction in pH within vesicle 190. In some embodiments, therapeutic agent 150 may be coupled to nanoparticle 100 by a pH-sensitive or acid-labile bond that is disrupted in acidic conditions (e.g., at ~pH 5.5).

Thus, a nanoparticle may be designed with targeting molecules to selectively target cells expressing a surface molecule and to deliver a therapeutic agent to the target cells. In some embodiments, the targeting molecule may bind to a surface molecule required for cellular adhesion. Nanoparticles configured to engage in multiple low affinity interactions with a target cell may better distinguish one cell type from another, resulting in improved selectivity. Therefore, the targeting molecules of a nanoparticle may be peptides selected for a broad range of binding affinities. Methods described herein may be used to construct nanoparticles with a desired ratio of targeting molecules to other components. Such methods allow the production of nanoparticles with a desired valence of the targeting molecules, and minimal batch-to-batch variation. Constructing nanoparticles with tightly controlled numbers/valences of targeting molecules may allow for optimization of multivalent interactions with the target cell for improved binding affinity and specificity of ligand-receptor interactions.

In some embodiments, a multifunctional nanoparticle may include a targeting component configured to bind to target surface receptors of a multiple myeloma (MM) cell and a therapeutic component configured to inhibit the survival of the MM cell. The binding of the targeting component to the target surface receptors may reduce or overcome cell adhesion mediated drug resistance (CAM-DR) in the MM cell, thereby preserving or enhancing the efficacy of the therapeutic component. Specific examples of this embodiment are described in further detail below.

VLA-4-mediated adhesion of multiple myeloma (MM) cells to the bone marrow stroma confers MM cells with cell-adhesion-mediated drug-resistance (CAM-DR). In the examples described below, micellar nanoparticles were used as dynamic self-assembling scaffolds to present VLA-4-antagonist peptides and doxorubicin conjugates simultaneously to selectively target MM cells and to overcome CAM-DR. Very late antigen-4 (VLA-4; also known as α4 μl integrin) is a cell surface heterodimer expressed on cancers of hematopoietic origin such as lymphomas, leukemias, and MM. In MM, VLA-4 is a key adhesion molecule that acts as a receptor for the extracellular matrix protein fibronectin and the cellular counter-receptor VCAM-1 (expressed on the BM stromal cells). VLA-4 plays a critical role in CAM-DR of MM cells and provides resistance to first line chemotherapeutics such as doxorubicin (Dox). Importantly, inhibition of MM cell adhesion to the BM microenvironment via a4-integrin blocking antibodies or a4-siRNA overcomes drug resistance in MM cells.

Enhanced accumulation of nanoparticles may be observed in tumor tissue due to the leaky vasculature found in the angiogenic vessels seen predominantly in solid tumors. Recent evidence in research has established that angiogenesis also plays a major role in some hematologic malignancies including MM. In line with these findings, liposomal doxorubicin (Doxil) has shown beneficial clinical outcome in MM patients when used in combination with vincristine and dexamethasone (VAD therapy), and has recently been FDA approved in combination with bortezomib in the treatment of relapsed or refractory MM. Despite the establishment of angiogenesis in MM, and demonstrated benefits of nanomedicine, the advantages nanoparticle based therapeutics can provide is yet to be harnessed to its full potential in MM.

PEGylated micellar nanoparticles offer a combination of increased stability, high circulation times, and a defined size range of 10-100 nm for increased tumor accumulation and decreased systemic toxicity. An important feature of micellar nanoparticles is that they present particularly attractive scaffolds for multivalent display as they can be designed to have multiple functional groups on their surfaces to present targeting moieties and drug conjugates simultaneously.

In the examples below, doxorubicin was conjugated to the nanoparticles through an acid-sensitive hydrazone bond to prevent premature release and thus non-specific toxicity. Peptides were conjugated via a multifaceted synthetic procedure for generating precisely controlled number of targeting functionalities per nanoparticle. The nanoparticles exhibited a size of ~20 nm, were efficiently internalized by MM cells, and induced cytotoxicity against MM cells. Mechanistic studies revealed that nanoparticles induced DNA double strand breaks and induced apoptosis, associated with H2AX phosphorylation, PARP and caspase-8 cleavage. Importantly, multifunctional nanoparticles were more efficacious than doxorubicin in the presence of fibronectin (IC50=0.15±0.04 μM and 0.42±0.09 μM, respectively), and overcame CAM-DR induced by adherence of MM cells to fibronectin. Finally, in a MM xenograft model, nanoparticles preferentially homed to MM tumors, with a ~10 fold more drug accumulation when compared to doxorubicin, and demonstrated dramatic tumor growth inhibition with much reduced overall systemic toxicity.

Thus, the disease-driven engineering of a nanoparticle-based drug delivery system may enable an integrative approach in the treatment of MM. Described below are specific examples of self-assembling multifunctional micellar nanoparticles for targeted delivery of Dox to MM cells while overcoming CAM-DR. This is accomplished by designing particles that are simultaneously functionalized with controlled numbers of VLA-4-antagonist peptides and pH sensitive Dox conjugates. When the nanoparticles are delivered, first they target VLA-4 expressing MM cells and inhibit cellular adhesion via VLA-4, thereby overcoming CAM-DR. At the same time, nanoparticle binding to VLA-4 triggers receptor-mediated uptake, upon which active Dox is released due to pH-sensitive bond hydrolysis in the acidic endocytic vehicles. These examples demonstrate the disease-driven engineering of a nanoparticle-based drug delivery system, enabling the model of an integrative approach in the treatment of MM.

Figure 5:
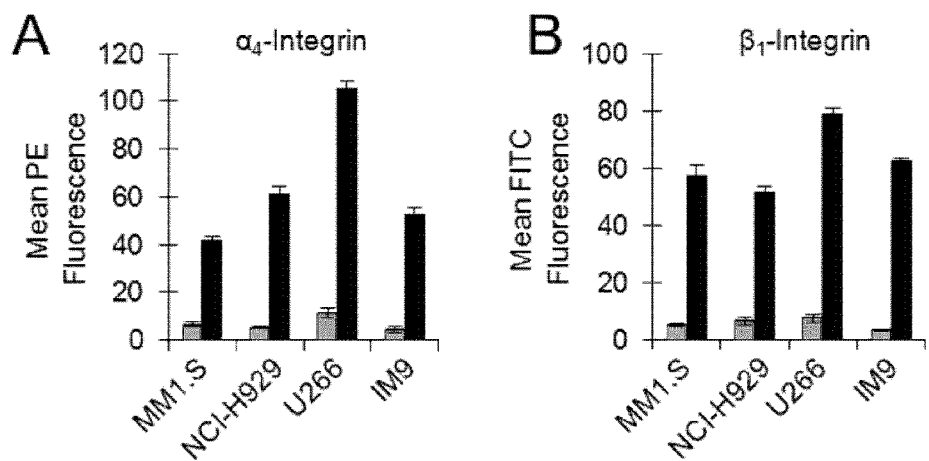
FIGS. 5a-5b illustrate expression of VLA-4 subunits α4- and β1-integrins in MM.1S, NCI-H929, U266, and IM9 cell lines, as determined by flow cytometry.

Example 1: Identification of a VLA-4 Antagonist Peptide that Selectively Binds to MM Cells and Inhibits MM Cell Adhesion to Fibronectin MM cells express VLA-4 (α4β1 integrin) receptor that facilitates adhesion of MM cells to the extracellular matrix protein fibronectin, thereby actuating CAM-DR development in MM cells. In several MM cell lines, including NCI-H929, IM9, U266, and MM.1S, VLA-4 expression was validated by detecting the expression of α4- and β1-subunits using flow cytometry. Both subunits were expressed on all cell lines tested (FIG. 5A).

VLA-4 is a cell surface receptor that plays a critical role in cancers as well as autoimmune diseases, and several VLA-4 targeting peptides have been identified. None of these peptides, however, have been tested for their specific binding to MM cells, or their antagonistic effects for inhibiting cellular adhesion. Since both these criteria are crucial in this targeting strategy, a small library of peptides was generated and screened from the literature.

For cellular binding assays we synthesized FITC labeled version of the peptides and compared their affinity to MM cells by flow cytometry.

Figure 6:
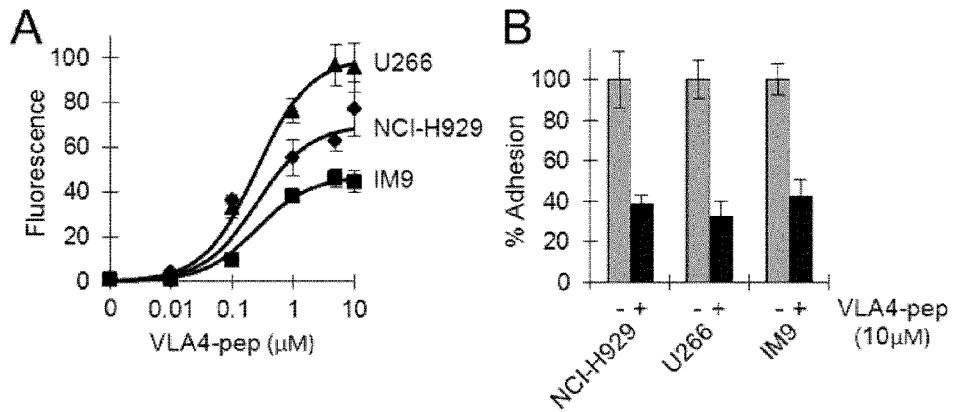
FIGS. 6a-6b illustrate binding of VLA-4-pep to U266, NCI-H929, and 1M-9 cell lines with apparent $K_d$ of ~250 nM (FIG. 6a) and inhibition of adhesion of MM cell lines to fibronectin-coated plates by VLA-4-pep (FIG. 6b)

VLA-4-pep binds to MM cells and inhibits their adhesion to fibronectin. As shown in FIGS. 5a-5b, MM.1S, NCI-H929, U266, and IM9 cell lines all express VLA-4 subunits α4- and β1-integrins as determined by flow cytometry. Black columns are primary antibodies, and grey columns are isotype controls. FIG. 6a shows the results of cellular binding assays performed using FITC-labeled VLA-4-pep and detected by flow cytometry. Control experiments were done with FITC-labeled non-specific peptide and the background binding was subtracted for each data point. VLA-4-pep binds to U266, NCI-H929, and 1M-9 cell lines with apparent Kd of ~250 nM. As shown in FIG. 6b, VLA-4-pep inhibits adhesion of MM cell lines to fibronectin-coated plates. BSA coated plates were used as controls, and no adhesion of MM cells was observed. No inhibition of adhesion was observed in the control experiments done with non-specific peptide (results not shown). All experiments were done in triplicates and data represents means (±SD).

Figure 4:
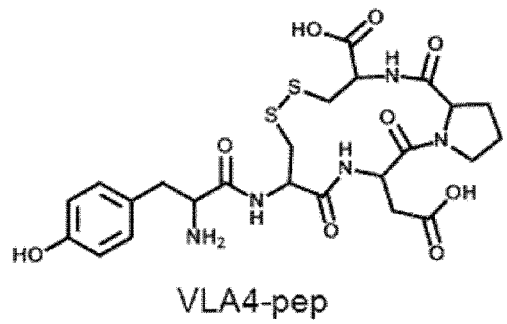
FIG. 4 illustrates the structure of VLA-4 antagonist peptide (VLA-4-pep)

We found that peptide-[9] (VLA-4-pep; SEQ ID NO: 1; FIG. 4) binds to MM cell lines with specificity (FIG. 6a). Control experiments done with FITC labeled non-specific peptide showed only minimal background binding, and was subtracted for each data point. Competition experiments done with excess unlabelled VLA-4-pep showed inhibition of fluorescence signal, indicating that VLA-4-pep specifically binds to VLA-4 receptor on MM cells (results not shown). VLA-4-pep also prevailed as the most potent inhibitor of MM cell adhesion to fibronectin in a typical calcein-based cell adhesion assay (FIG. 5b). Control experiments done with non-specific peptide did not show any adhesion inhibitory effects (results not shown). Therefore, in our hands, VLA-4-pep prevailed as leading VLA-4 antagonist peptide and was incorporated as the targeting moiety in the nanoparticles.

Another of the candidates we tested (the peptide sequence CFLDFP) had a weaker affinity for VLA-4. This sequence could be substituted for VLA-4-pep as a targeting molecule in nanoparticles for treating MM. Peptide sequences based on the X-CDPC core structure, where X is a variable amino acid, could also be substituted for VLA-4-pep as a targeting molecule in nanoparticles for treating MM.

Example 2: Synthesis of VLA-4-pep and Dox Conjugated Lipids and Nanoparticles

Peptides, and peptide/DSPE-PEG2000 lipid conjugates with fluorescence moieties were manually synthesized on solid support, rink amide resin, using Fmoc chemistry (peptide synthesis chemicals/reagents from NovaBiochem, DSPE-PEG2000 from Avanti Lipids Inc.). Resin cleavages of all peptide products were done by TFA, purification via RP-HPLC, and characterization by MALDI-TOF-MS. Peptide cyclization through disulfide bond formation between cysteine residues was performed in 1 mL DMF with 20 µL DIEA by stirring for 8 hrs at room temperature. DPPE-GA, hydrazine, and diisopropylcarbodiimide were mixed in a vial and allowed to react for 4 hours at room temperature. Solvent and excess reactants were removed via evaporation under vacuum. Product was re-dissolved in chloroform, mixed with Doxorubicin in methanol and coupled over 3 days. Final product was isolated via extraction, and characterized with MS.

Figure 7:
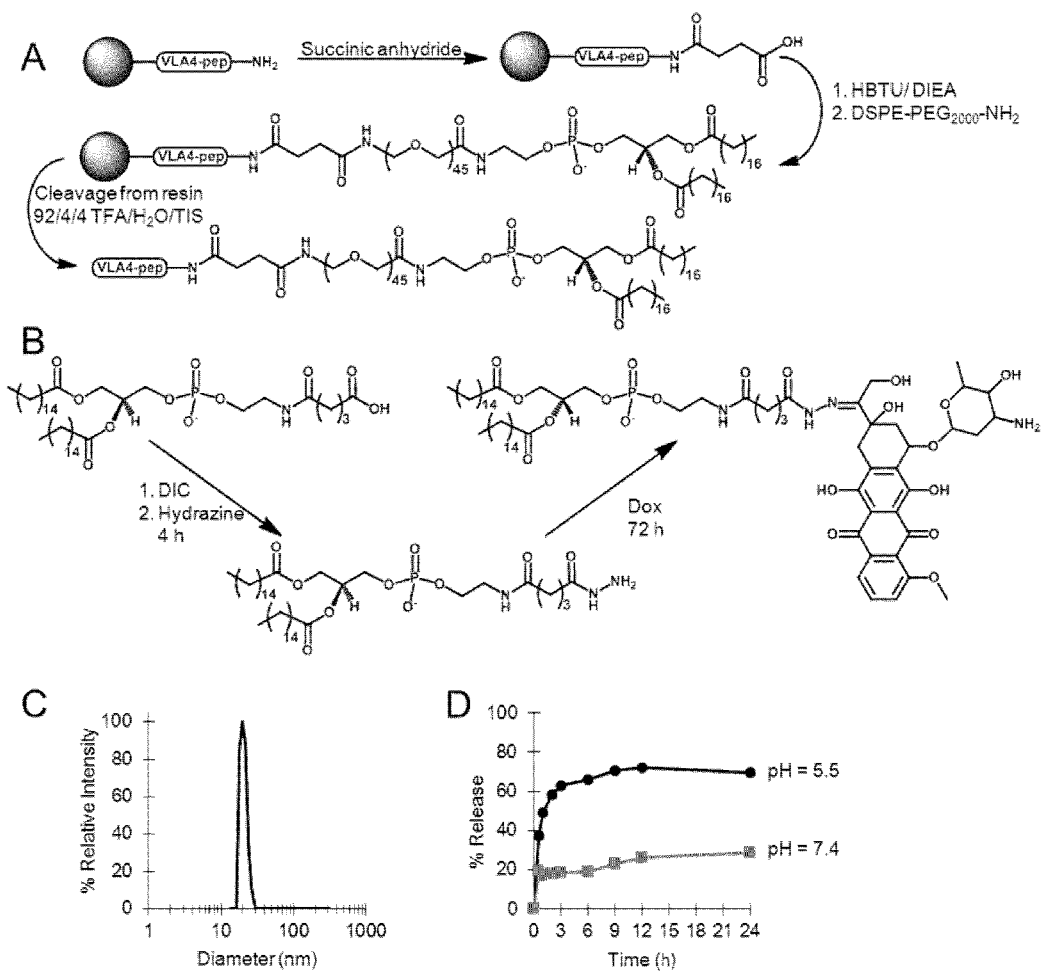
FIGS. 7a-7d illustrate synthesis and characterization of VLA-4 targeting, Dox conjugated multifunctional nanoparticles (NPDox/VLA-pp)

The VLA-4 targeting peptide, VLA-4-pep, was incorporated on the nanoparticle for active targeting of MM cells. VLA-4-pep/DSPE-PEG2000 conjugate was synthesized using a synthetic strategy that was developed using solid support methodology. FIG. 7a is a schematic illustration of the multifaceted synthetic steps for peptide conjugation to DSPE-PEG2000-NH2 using this solid support methodology. VLA-4-pep was first synthesized on the rink amide resin using Fmoc protocols, followed by reacting succinic anhydride at the N-terminal amine to generate a carboxylic acid group at the peptide terminus. This newly generated carboxylic acid group on the resin bound peptide was activated, and DSPE-PEG2000-Amine lipid was introduced in anhydrous DMF to promote amide coupling. The peptide-PEG-lipid conjugate was cleaved from the resin using a TFA cocktail, purified via HPLC and characterized by MALDI-TOF-MS.

Dox/DPPE-GA lipid conjugation was accomplished using a pH sensitive hydrozone chemistry to provide controlled drug release. FIG. 7b is a schematic illustration of Dox conjugation to DPPE-GA.

Nanoparticles were synthesized from the lipid-PEG block co-polymer, DSPE-PEG2000. This PEG-lipid, when placed in water, self-assembles to form micelles with 16 nm diameter. Their size stipulates the EPR effect, and prevents their entry through healthy endothelium pores. Meanwhile, the PEG conjugation increases micellar solubility and biocompatibility, provides the nanoparticles with stealth against the reticuloendothelial system and increases their circulation time. DSPE-PEG2000 lipid has a low CMC (5-10 µM) allowing for experimentation at therapeutically relevant concentrations without lipid dissociation. DSPE-PEG2000 also has a terminal primary amine allowing for easy conjugation of various different molecular moieties.

Multifunctional micelles were prepared by mixing DSPE-PEG2000, VLA-4-pep/DSPE-PEG2000 conjugate, and Dox/DPPE-GA conjugate at desired molar ratios in DCM, followed by solvent removal via evaporation. The mixture was then re-suspended in PBS, and stirred until clear Each micelle comprises ~90 lipid molecules, and their relative monodispersity allows for incorporation of precise numbers of functionalized lipids per particle to provide control over valency of targeting peptide and drug loading.

Besides VLA-4 targeting, Dox conjugated multifunctional nanoparticles (NPDox/VLA-4-pep), only Dox conjugated (NPDox), only VLA-4-pep conjugated (NPVLA-4-pep), Dox and non-specific peptide conjugated (NPDox/ns), non-specific-peptide conjugated (NPns), and bare nanoparticles (NPbare) was prepared for control experiments. For imaging and cellular uptake experiments, lissamine rhodamine PE was incorporated in the micelles during formation. In all experiments the total lipid concentration was above CMC.

Particle size was observed using dynamic light scattering analysis via the 90Plus Nanoparticle Size Analyzer (Brookhaven Instruments Corp.), using 658 nm light observed at a fixed angle of 90° at 20° C. All samples were centrifuged for 30 minutes before analysis to eliminate dust and larger aggregates. FIG. 7c illustrates dynamic light scattering (DLS) analysis of the nanoparticles. The DLS analysis established that regardless of the number and type of functional moieties included, the particles maintained their original size of ~20 nm. VLA-4 targeting, Dox conjugated (NPDox/VLA-4-pep), only Dox conjugated (NPDox), only VLA-4-pep conjugated (NPDox/VLA-4-pep), Dox and non-specific peptide conjugated (NPDox/ns), nonspecific-peptide conjugated (NPns), and bare nanoparticles (NPbare) all gave an average size distribution around 20 nm (FIG. 7c).

Dox was conjugated to the nanoparticles via an acid labile bond to prevent the premature release of the chemotherapeutic and thus non-specific toxicity. Upon endocytosis of nanoparticles, the acidic environment of endosomes catalyzes the release of active Dox, providing localized delivery inside tumor cells. To analyze the Dox release kinetics, Dox conjugated nanoparticles ([Dox]=34.5 µM) were prepared and release rates were analyzed at pH=7.4 PBS buffer, pH=5.5 acetate buffer, and 0.24N HCl. Amounts of free Dox for all buffers at different time points were measured using a Toyopearl AF-Amino-650M resin (Tosoh, Tokyo, Japan) packed column on Agilent series 1200 HPLC according to absorbance at 477 nm. All data was normalized to total Dox released in HCl solution where hydrolysis is 100% within ~5 minutes.

FIG. 7d illustrates the drug release profile of Dox from the nanoparticles at pH=5.5 and pH=7.4. Rate of hydrolysis was quantified via HPLC, taking measurements at pre-determined time intervals and observing the absorbance at wavelength of 477 nm. Data shown are from a representative experiment. The drug release profiles we observed in pH 7.4 and pH 5.5 established that Dox is released from the nanoparticles preferentially under acidic conditions (FIG. 7d).

Example 3: Cellular Uptake Studies of VLA-4 Targeting Nanoparticles

Next we evaluated whether VLA-4-pep functionalized nanoparticles were taken up by VLA-4 expressing MM cells and determined the optimal peptide valency per micelle for most efficient uptake profiles. All MM cell lines were obtained from ATCC, and were cultured as previously described. Methods are described in detail below.

Detection of α4- and β1-integrin subunit expression: cells were stained with anti-CD49d(PE) or anti-CD29 (FITC) antibodies (BD Biosciences). Isotype matched antibodies were used as negative controls. For detection of apoptotic cells, cells were stained with Annexin V (FITC) antibody (BD Pharmingen). Cells were analyzed with Guava EasyCyte flow cytometer (Millipore).

Cell-binding assays: MM cells were incubated on ice, for 1 h, with FITC-labeled peptides in binding buffer (25 mM Tris, 150 mM NaCl, 1.5 mM $MgCl_2$, 1.5 mM $MnCl_2$, 5 mM glucose, 1.5 mM BSA). Cells were washed twice with PBS and were analyzed with Guava EasyCyte flow cytometer (Millipore). FITC-labeled scrambled peptide was used as a non-specific control, and was subtracted for each data point.

Adhesion Assays: These were performed using the Vybrant Cell Adhesion Assay Kit (Molecular Probes) according to the manufacturer's instructions. Briefly, calcein-labeled MM cells were added to fibronectin-coated 96 well plates (40 μg/ml) in adhesion buffer (RPMI-1640/2% FBS) for 2 h. To evaluate the adhesion inhibitory effects of VLA-4-pep or VLA-4-pep functionalized nanoparticles, calcein labeled cells were added to fibronectin-coated plates, and immediately treated with the inhibitory agents. Nonadherent cells were removed by washing twice with PBS. Adherent cells were quantitated in a fluorescence multi-well plate reader.

Cellular Uptake studies: MM cells were incubated at 37° C. with rhodamine-labeled nanoparticles in complete media for the indicated time points and were analyzed with Guava EasyCyte flow cytometer. For confocal microscopy experiments, cytospin of nanoparticle-treated cells were prepared on glass slides and fixed with 4% paraformaldehyde. Coverslips were then mounted on the glass slides with VectaShield antifade/DAPI (Vector Labs). Cells were visualized by Nikon A1R confocal microscope with a 40× oil lens. Image acquisition was performed by Nikon Elements Ar software (Nikon).

Figure 8:
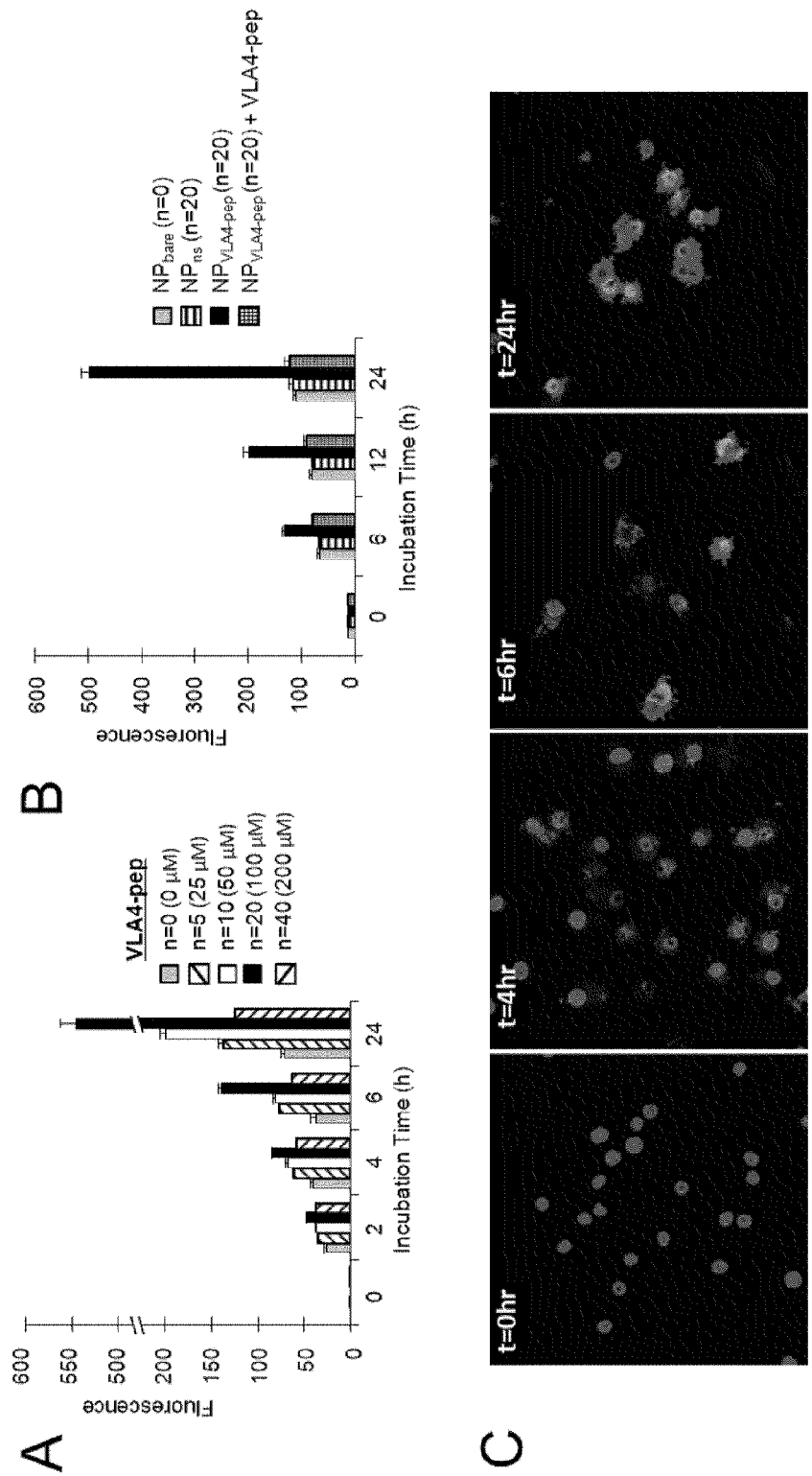
FIGS. 8a-8c illustrate cellular uptake studies with drug delivery nanoparticles.

Cellular uptake of rhodamine-labelled nanoparticles with varying number of VLA-4-pep conjugates (n=0-40/nanoparticle) were studied via flow cytometry. FIGS. 8a-8c illustrate the results of cellular uptake studies. Referring first to FIG. 8a, rhodamine-labeled nanoparticles with varying valency of VLA-4-pep conjugates (n=0-40/nanoparticle) were prepared and incubated with NCI-H929 cells at 37° C. for the indicated time points. Nanoparticle uptake by NCI-H929 cells increased with increasing VLA-4-pep valency up to n=20, however dropped dramatically at n=40 (FIG. 8a). Specifically, we observed that 20 peptides per particle yielded the maximum uptake, with up to 10 fold enhancement over that of non-targeted micelles (n=0) after 24 h.

In a separate experiment, we also used nanoparticles conjugated with non-specific peptide (n=20) as a control, and observed similar results to that of non-targeted nanoparticles (FIG. 8b). Control experiments with non-specific peptide conjugated nanoparticles (NPns) and competition experiments with excess free VLA-4-pep (2 mM) were performed to determine receptor-mediated specificity of nanoparticle uptake. Data presented in FIG. 8b represents means (±SD) of triplicate experiments.

To establish that uptake of VLA-4-pep conjugated particles were receptor-mediated, we performed competition experiments, where MM cells were co-incubated with VLA-4-pep conjugated nanoparticles (n=20) and excess free VLA-4-pep. As shown in FIG. 8c, the internalization of VLA-4 targeting nanoparticles was confirmed with a Nikon A1R confocal microscope using a 40× oil lens. Image acquisition was performed by Nikon Elements AR software. The results showed a dramatic reduction in cellular uptake back to the levels of non-targeted nanoparticles, proving receptor involvement in uptake (FIG. 8c). It is noteworthy that we observed some nanoparticle uptake even with non-targeted micelles indicating low levels of non receptor-mediated uptake (FIG. 8a,b).

The studies described above were performed using flow cytometric analysis, as it is a highly accurate quantitative method for studying the effect of peptide valency on uptake. One shortcoming of this method, however, is that it does not discriminate surface bound nanoparticles from internalized ones. Therefore, to show that the nanoparticles are indeed internalized by MM cells, we performed confocal microscopy experiments. These experiments revealed clear uptake of VLA-4-pep conjugated nanoparticles starting around 4 h and peaking at 24 h (FIG. 8c). Altogether, these studies showed efficient receptor-mediated uptake of nanoparticles with optimal uptake properties of n=20 VLA-4-pep per micelle. Therefore valency of 20 peptides per particle was used for rest of our studies.

Example 4: Multifunctional Nanoparticles are Cytotoxic to MM

We evaluated the cytotoxicity of NPDox/VLA-4-pep nanoparticles against NCI-H929 MM cells using a colorimetric assay as follows.

Cytotoxicity assays: Cytotoxicity was determined using Cell Counting Kft-8 (Dojindo) as previously described. To determine cytotoxicity in the presence of fibronectin, MM cells were plated on fibronectin coated plates (40 μg/ml), in adhesion buffer, for 1 h. Cells were then treated with increasing concentration of nanoparticles or free Dox (equivalent Dox concentrations of NPDox/VLA-4-pep, NPDox, or free Dox) in complete media with 10% FBS, for 48 h and 72 h. BSA coated plates were used as controls. In all cases, cell viability was assessed by cell counting kit-8 (CCK-8), and data represent means (±SD) of triplicate cultures. The results are shown in FIG. 9.

Figure 9:
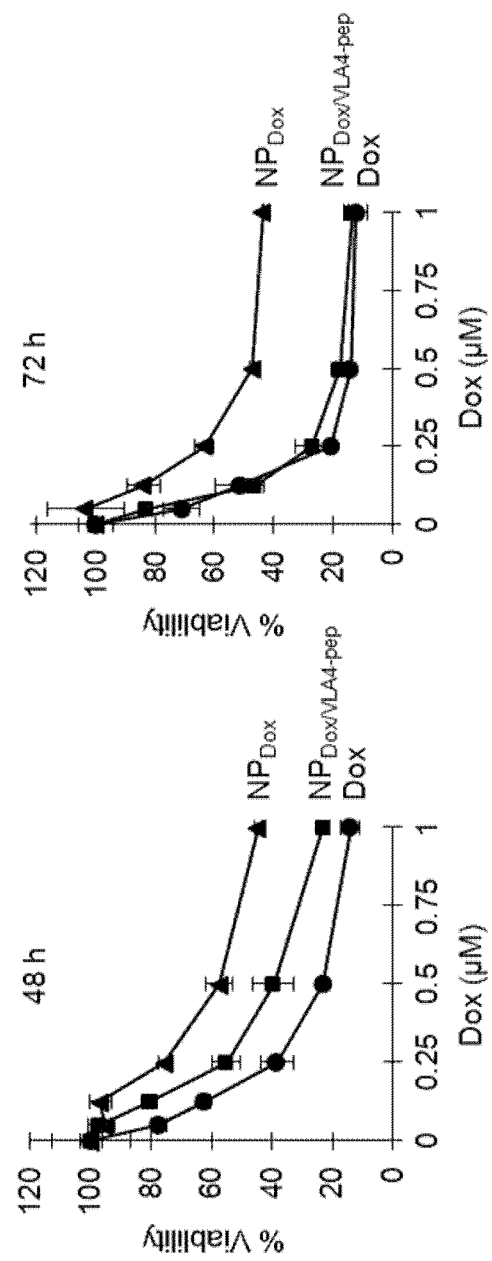
FIG. 9 illustrates induction of cytotoxicity in MM cells by NPDox/VLA-4-pep.

NPDox/VLA-4-pep was significantly cytotoxic to MM cells with $IC_{50}$ values of 0.39±0.06 μM (48 h), and 0.13±0.02 μM, at 48 and 72 h, respectively (FIG. 9). Control experiments performed with equivalent doses of free Dox showed a moderate advantage to NPDox/VLA-4-pep at 48 h ($IC_{50}$=0.19±0.04 μM). This difference was diminished at 72 h, and both free Dox and NPDox/VLA-4-pep showed similar cytotoxic effects ($IC_{50}$=~0.13 μM). The difference in cytotoxicity at 48 h is expected given the differences in the cellular uptake mechanisms of free Dox and NPDox/VLA-4-pep. While free Dox is taken up via passive diffusion and is active immediately, we designed our nanoparticles to release active Dox only after they are internalized and are exposed to the acidic environment of the endocytic vesicles. These differences would lead to the temporal difference observed in cytotoxicity. Control experiments done with non-targeted NPDox showed much reduced cytotoxic effects at 48 and 72 h, further confirming VLA-4's role in nanoparticle uptake (FIG. 9). Control experiments done with nanoparticles conjugated with non-specific peptide (NPDox/ns) yielded very similar results to those obtained with non-targeted NPDox (results not shown). Control experiments performed with NPDox/ns showed similar results to NPDox and NPbare, and NPVLA-4-pep did not show any cytotoxic effects at the concentrations tested (results not shown). No cytotoxic effects were observed in additional control experiments performed with nanoparticles lacking Dox conjugates, such as NPbare or NPVLA-4-pep, at equimolar particle concentrations (results not shown).

Figure 10:
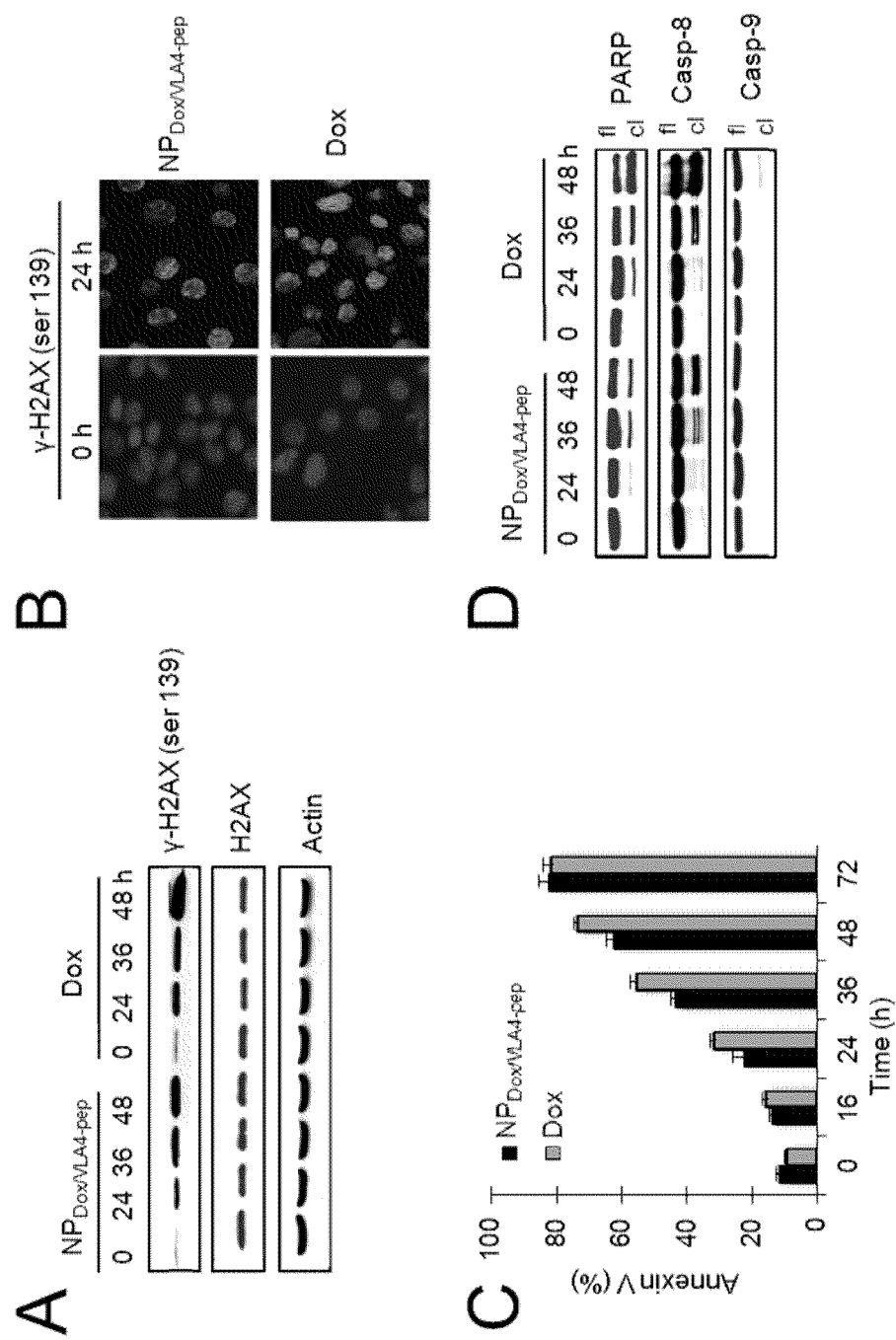
FIGS. 10a-10d illustrate induction of DNA DSBs and apoptosis in MM cells by NPDox/VLA-pep.

Example 5: Multifunctional Nanoparticles Induce DNA Double Strand Breaks (DSBs) and Apoptosis in MM Cells It is well established that Dox induces DNA double strand breaks (DSBs) and apoptosis of cancer cells. An early specific cellular response to DSBs in mammalian cells is the phosphorylation of the histone protein H2AX (γ-H2AX), with respective foci formation. Therefore, we examined whether free Dox and NPDox/VLA-4-pep triggered similar signaling cascades of DNA damage and apoptosis in MM cells. NCI-H929 cells were treated with 250 nM Dox equivalents of NPDox/VLA-4-pep or free Dox for 0-48 h. Phosphorylation of DNA damage response protein H2AX at Ser139 was assayed by western blotting (FIG. 10a). Respective H2AX foci formation was assayed by immunocytochemistry (FIG. 10b). Apoptosis was assessed by flow cytometry following Annexin V-FITC staining (FIG. 10c), and by western blotting for PARP cleavage and caspase-8 and caspase-9 activation (FIG. 10d).

For immunocytochemistry analysis, cytospins of drug-treated cells were prepared on glass slides and fixed with 4% paraformaldehyde. Slides were blocked with 5% goat serum, incubated with y-H2AX antibody (Cell Signaling) overnight at 4° C., and then with AlexaFluor-488-labelled Fab2 (Molecular Probes). Coverslips were then mounted on the glass slides with VectaShield antifade/DAR (Vector Labs) and analyzed by Nikon Eclipse TS100 fluorescence microscope at 60×/0.5-1.25 oil, with a Nikon Infinity camera. For flow cytometry analysis, data represent means (±SD) of triplicate experiments. For western blotting, representative images are shown, and all antibodies were purchased from Cell Signaling.

Western blot and immunocytochemical analysis showed that both free Dox and NPDox/VLA-4-pep induced H2AX phosphorylation in NCI-H929 cells (FIGS. 10a, b). Furthermore, both agents induced apoptosis as was detected by flow cytometric analysis of the early apoptotic marker annexin V (FIG. 10c), and western blot analysis of PARP and caspase-8 activation (FIG. 10d). No significant caspase-9 activation was detected by either agent. Altogether, these results suggest that free Dox and NPDOX/VLA-4-pep exert their cytotoxic effects through the similar cytotoxic mechanisms. It is noteworthy that no cell death or caspase activation was detected before 36 h at these doses. Therefore, formation of DSBs was not a secondary event of apoptosis.

Example 6: Multifunctional Nanoparticles Inhibit Adhesion of MM Cells to Fibronectin & Overcome CAM-DR VLA-4-pep serves two major purposes in our nanoparticle design: i) selective targeting of VLA-4 expressing MM cells, and ii) inhibition of MM cell adhesion to the stroma to overcome CAM-DR. To test whether NPDox/VLA-4-pep overcame CAM-DR, first we evaluated its efficiency in inhibiting MM cells' adhesion to fibronectin. Calcein-labeled NCI-H929 MM cells were allowed to adhere to fibronectin coated plates alone, or with increasing concentrations of NPVLA-4-pep. Non-adherent cells were removed by washing with PBS, and adherent cells were quantitated in a fluorescence multi-well plate reader. Data represents means (±SD) of triplicate experiments. *P<0.05, **P<0.01 when compared to control. Dox was not incorporated to the nanoparticles during this assay to eliminate compounding effects that would result from cell death. No inhibition of adhesion was observed with NPbare or NPns (results not shown). NPVLA-4-pep inhibited adhesion of calcein-loaded NCI-H929 cells to fibronectin in a dose dependent manner (FIG. 11a).

Next, we compared the cytotoxic effects of free Dox and NPDox/VLA-4-pep against MM cells in the presence or absence of fibronectin. NCI-H929 cells were allowed to adhere to fibronectin or BSA coated plates for 1 h, and then treated with equivalent Dox concentrations of NPDox/VLA-4-pep, or free Dox for 72 h. Fibronectin coated plates were used to allow for adhesion of NCI-H929 cells, and BSA coated plates were used for culturing cells in suspension (MM cells do not adhere to BSA coated plates). Cell viability was assessed by cell counting kit-8 (CCK-8), and data represent means (±SD) of triplicate cultures. Adhesion of NCI-H929 cells to fibronectin caused CAM-DR in the free Dox treatment group with a 3-fold IC50 shift from 0.13±0.04 µM to 0.42±0.09 µM (FIG. 11b, left). In the NPDox/VLA-4-pep treatment group, however, the $IC_{50}$ values merged towards ~0.2 µM both for the adherent and suspension MM cells, indicating that NPDox/VLA-4-pep overcame CAM-DR (FIG. 11b, right).

The significance of these findings is best illustrated in FIG. 11c, which shows an alternative view of data presented in FIG. 11b. When MM cells are cultured in suspension, the efficacy of free Dox in cell killing is similar to that of NPDox/VLA-4-pep with an $IC_{50}$=~0.13 µM (FIG. 11c, left). On the other hand, when the cells are cultured in the presence of fibronectin, NPDox/VLA-4-pep ($IC_{50}$=0.15±0.04 µM) is more efficacious than free Dox ($IC_{50}$=0.421-0.09 µM). These results suggest that NPDox/VLA-4-pep overcomes CAM-DR in MM cells.

Example 7: Multifunctional Nanoparticles Preferentially Home to MM Tumors and Inhibit Tumor Growth In Vivo FIGS. 12a-12f illustrate the in vivo characterization of NPDox/VLA-4-pep in a subcutaneous xenograft model of MM. To validate the therapeutic efficacy of multifunctional nanoparticles, CB.17 SCID mice (Harlan Laboratories) were irradiated with 150 rad, and were inoculated subcutaneously with 5×10$^6$ NCI-H929 cells. The SCID mice were randomly distributed into 4 treatment groups of 8 mice: i) free Dox (6 mg/kg), ii) NPDox/VLA-4-pep (6 mg/kg Dox equivalent), iii) NPDox (6 mg/kg Dox equivalent), and iv) PBS (vehicle control). When the tumors were palpable, each mouse was injected with the drug, intravenously, on days 1, 3, and 5. Tumor bearing SCID mice were injected, iv) with free Dox, NPDox/VLA-4-pep, or NPDox, at a dose of 6 mg/kg Dox equivalents on days 1, 3 and 5. Animals were monitored for body weight and tumor volume by caliper measurements. Tumor growth inhibition was detected by caliper measurements (left). Data shown are means (±SE) of n=6-8 per treatment group. Statistical comparisons of continuous variables were carried out by Student's two-tailed t-test and were considered significant when P<0.05.

For determination of systemic toxicity, 3 additional mice from each group were sacrificed on day 5 before any lethality was observed. Organ weights were measured. For complete blood count analysis, 200 µl of blood was drawn from each mouse via cardiac puncture, immediately mixed with 50 µl of Sequester Solution (Cambridge Diagnostic Products), and was analyzed with the HemaVet950 (Drew Scientific). Immunohistochemical staining of excised tumors for caspase-3 was performed as previously described.

Figure 12:
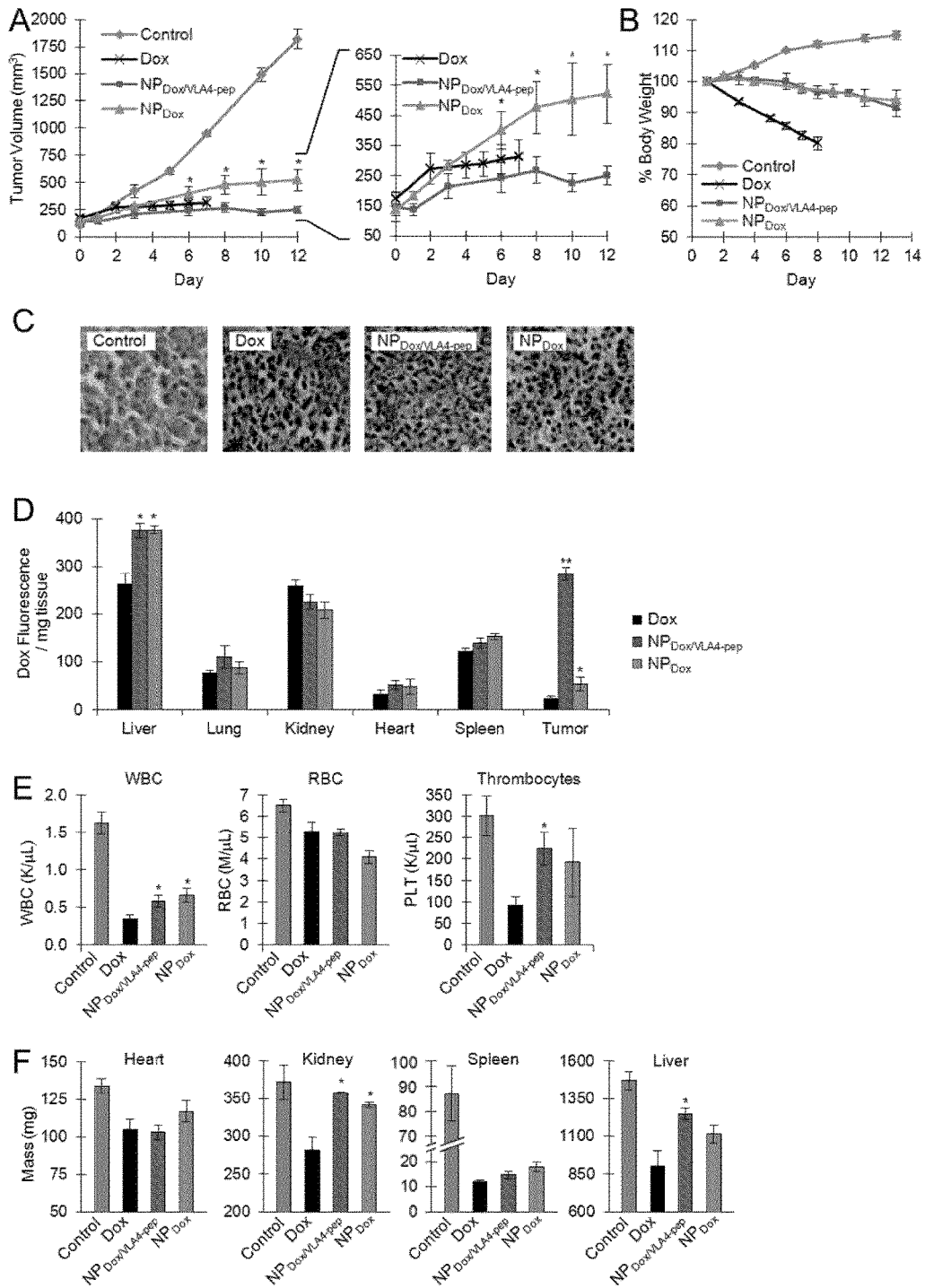
FIGS. 12a-12f illustrate in vivo characterization of NPDox/VLA-4-pep in a subcutaneous xenograft model of MM.

The results are shown in FIGS. 12a-12f. As indicated, both free Dox and NPDox/VLA-4-pep resulted in dramatic tumor growth inhibition (FIG. 12A). However, at the dose used, free Dox resulted in a significant loss of body weight, and caused lethality of all mice on day 7 because of high systemic toxicity (FIG. 12b, % body weight of animals as a measure of systemic toxicity). Only 5% loss was observed with NPDox/VLA-4-pep or NPDox. The NPDox/VLA-4-pep group only lost 5% body weight and no lethality was observed during the duration of the study (FIG. 12b). NPDox/VLA-4-pep was significantly more efficacious than NPDox with *P<0.05 (FIG. 12a, right). These results indicate that NPDox/VLA-4-pep has a much-improved therapeutic index when compared to free Dox. NPDox also showed tumor growth inhibition, but was significantly less efficacious than NPDox/VLA-4-pep (FIG. 12a, right).

Three mice from each group were dissected on day 5 and tumors were stained for activated caspase-3. Representative images of tumor cross-sections that were captured using a Nikon Eclipse TS100 microscope at 20× magnification are shown. Ex-vivo mechanistic studies performed on tumors dissected on day 5 showed that all drug treatment groups induced apoptosis associated with caspase-3 activation (FIG. 12c).

NPDox/VLA-4-pep can expectedly accumulate in the tumor through the enhanced permeation and retention (EPR), as well as the VLA-4 targeting functionality, resulting in reduced systemic toxicity. To evaluate enhanced tumor uptake, the tissue biodistribution of Dox was studied for all treatment groups. Three mice per group were dissected 24 h after injection with 10 mg/kg free Dox or Dox equivalent nanoparticles, processed as previously described, and analyzed by fluorescence spectroscopy for Dox fluorescence (ex. 490 nm/em. 550 nm).

Tissue biodistribution of Dox following treatment is shown in FIG. 12d. Data shown are means (±SE). *P<0.05, **P<0.01 when compared to free Dox group. No significant difference was detectable in the distribution of Dox in lung, kidney, heart, or spleen at 24 h, however, a very high accumulation of Dox was observed in the tumor for the NPDox/VLA-4-pep group when compared to free Dox and NPDox, reaching to ~10 and ~5 fold higher levels, respectively (FIG. 12d). These results are consistent with the enhanced tumor growth inhibition observed with NPDox/VLA-4-pep and demonstrate that incorporating VLA-4-pep to the nanoparticles enabled enhanced targeting of VLA-4 expressing MM tumors. Dox accumulation in the tumor was ~2 fold more for NPDox, when compared to free Dox.

To evaluate systemic toxicity, analysis of complete blood cell count, which is highly susceptible to chemotherapeutic agents, was performed. Three mice from each group were dissected on day 5, and complete blood count (white blood cell, red blood cell, and thrombocyte) was performed (FIG. 12e). Weights of excised heart, kidney, spleen and liver are shown in FIG. 12e. Data represents means (±SE). *P<0.05, when compared to free Dox group.

Systemic toxicity was detectable in all treatment groups as evident from white blood cell (wbc) red blood cell (rbc), and thrombocyte counts (FIG. 12e). NPDox/VLA-4-pep group, however, showed significantly less toxicity on wbc and thrombocyte counts when compared to free Dox (FIG. 12e).

Dox has been associated with clinically significant cardiac and renal toxicity. The effect of the nanoparticles on cardiac and renal weight loss was therefore evaluated. All treatment groups showed a mild reduction in cardiac mass, with no detectable difference between NPDox/VLA-4-pep and free Dex (FIG. 12f). Previous studies performed in animal models have shown that free Dox is significantly more toxic to cardiac tissue when compared to nanoparticles. The lack of such a differential in the results could be due to the relatively early time point (5 days) at which the analysis was performed. On the other hand, a significant difference on kidneys was detected, as NPDox/VLA-4-pep was significantly less toxic to the kidneys than free Dox and did not cause any significant renal mass loss (FIG. 12f).

It is noteworthy that, based on biodistribution studies, significant Dox accumulation was evident in kidneys in all treatment groups (FIG. 12d). It is possible that the reduced toxicity of the nanoparticles on kidneys is due to the acid sensitive hydrazone bond, which releases active Dox only after receptor-mediated uptake, or in the acidic microenvironment of the tumor tissue.

Nanoparticles are known to accumulate in and be cleared by the reticuloendothelial system (RES) organs (spleen/liver). Therefore, the effect of nanoparticles on spleen and liver was analyzed. All treatment groups, including free Dox, showed significant and similar accumulation in spleen (FIG. 12f) and severe mass loss (FIG. 12f). Histopathological examination of spleen revealed severe hypoplasia of both erthroid and myeloid elements in all drug treatment groups. Nanoparticles, however, showed only moderate fibrosis, whereas severe fibrosis was evident in the free Dox group. Although nanoparticles of ~100 nm diameter have been shown to differentially accumulate in spleen, the small size of our micellar nanoparticles (~20 nm) may provide a mechanism to escape the spleen compartment of RES, leading to similar accumulation and toxicity to free Dox. On the other hand, biodistribution studies suggested an increased accumulation of nanoparticles in liver (FIG. 12d), but with reduced mass loss than free Dox (FIG. 12f). Histopathological analysis of liver revealed moderate hepatocellular hypertrophy and degeneration in the free Dox group, whereas only mild effects were observed in the nanoparticle treatment groups. Increased accumulation to liver without increased toxicity was also shown in previous studies and could be due to the acid sensitive hydrazone bond, which requires receptor-mediated uptake or the acidic microenvironment of the tumor cells to release active Dox. Altogether these results indicate that NPDox/VLA-4-pep showed decreased overall systemic toxicity than free Dox.

In summary, in vivo studies demonstrated dramatic tumor growth inhibition, significantly increased accumulation in the tumor, and overall decreased systemic toxicity by NPDox/VLA-4-pep. Combined, the results suggest improved therapeutic index for NPDox/VLA-4-pep in comparison to free Dox.

In this study, multifunctional micellar nanoparticles were engineered that target VLA-4 expressing MM cells selectively, while combining cellular adhesion inhibitory effects and cytotoxic effects in a temporal fashion to overcome CAM-DR. In our design, peptides were used as targeting agents, which have several advantages over antibodies such as favorable pharmacokinetics, easy derivatizing and manufacturing, and lower cost. Another advantage is that, unlike antibody therapeutics that rely on high affinity interactions, peptides can be selected to have a broad range of binding affinities. In physiological systems, multiple low affinity interactions are used to distinguish one cell type from another and to provide selectivity. Multivalent presentation improves not only the binding affinity but also the specificity of ligand-receptor interactions.

A low affinity VLA-4 antagonistic peptide was selected for these studies ($K_d$~0.25 µM; FIG. 4), and micellar nanoparticles were used as dynamic self-assembling scaffolds to multivalently present this peptide to target VLA-4 overexpressing MM cells. Receptor-mediated endocytosis is a particularly important aspect in the design of the above-described examples of nanoparticles, since the acidic environment of the endocytic vesicles are required for active Dox release (FIG. 7d). The results demonstrated that binding of the nanoparticles to VLA-4 triggered receptor-mediated uptake. Interestingly, it was observed that the efficiency of uptake depended on the number of targeting peptides per micelle, with an optimal number of 20 peptides per micelle. While the optimal number of targeting peptides per micelle may vary based on the peptide's monovalent affinity, as well as its $k_{on}$ and $k_{off}$ rate constants, these studies validated VLA-4 as a suitable target for targeted drug delivery in MM.

Figure 11:
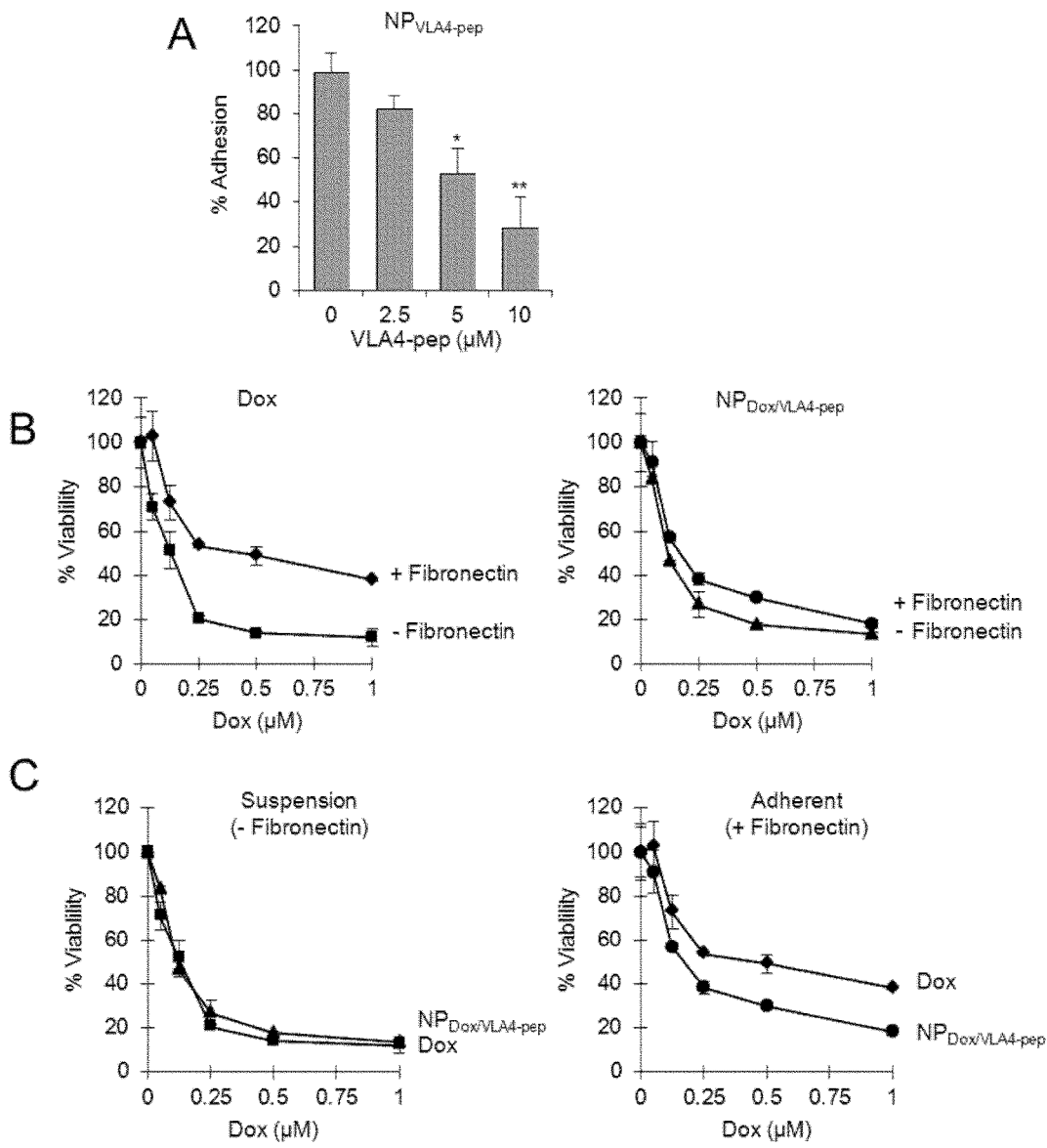
FIGS. 11a-11c illustrate inhibition of adhesion of MM cells to fibronectin and overcoming of CAM-DR by NPDox/VLA-4-pep.

One of the key findings of the study was the efficacy of NPDox/VLA-4-pep on MM cell cytotoxicity in the presence of the extracellular matrix protein fibronectin. When the cells are cultured in suspension, in the absence of fibronectin, the efficacy of free Dox in cell killing was similar to that of NPDox/VLA-4-pep. However, when the cells were allowed to adhere to fibronectin, NPDox/VLA-4-pep proved to be more efficacious than free Dox (FIG. 11). In other words, while adhesion of MM cells to fibronectin provided CAM-DR when cells were treated with free Dox, NPDox/VLA-4-pep significantly overcame CAM-DR. These results establish the significance of targeting MM cells as well as their interactions with the microenvironment in the design of more effective novel therapeutics.

Several different mouse models of MM were described. Here, a subcutaneous xenograft model of MM was used for various advantages this model provides, such as the formation of palpable tumors, which makes tumor growth inhibition and biodistribution studies feasible. In addition, tumors can be excised to enable ex-vivo mechanistic analysis. A key factor in drug delivery efficiency is the tumor-to-normal organ uptake ratios of the chemotherapeutic agents. The in vivo results demonstrated that NPDox/VLA-4-pep preferentially accumulates in the tumor when compared to free Dox and NPDox. Most importantly, NPDox/VLA-4-pep showed dramatic tumor growth inhibition with decreased overall systemic toxicity, demonstrating improved therapeutic index. It is noteworthy that VLA-4-pep targets human VLA-4, and that NPDox/VLA-4-pep may have a different toxicity profile in humans.

One shortcoming of the subcutaneous xenograft model is the growth of tumors in the lack of BM microenvironment. Therefore the growth and survival advantages provided by the microenvironment are not well recapitulated in this model. Given that the inhibition of CAM-DR effect of NPDox/VLM4-pep is best emphasized in the presence of the BM microenvironmental factors such as fibronectin (FIG. 11), the improvement of efficacy observed with NP Dox/VLA-4-pep using this model may be an underestimate. Thus, dosages and timing of administration of nanoparticles as described herein may be determined using known methods, and may vary among embodiments.

In summary, nanotechnology has been harnessed to develop a "one stone, two bird" combinational therapy approach for MM, where Dox conjugated nanoparticles selectively targeted VLA-4 expressing MM cells, prevented development of CAM-DR, and dramatically inhibited tumor growth with overall reduced systemic toxicity. Taken together, this study provides the preclinical rationale for the clinical evaluation of VLA-4 targeting, Dox conjugated multifunctional nanoparticles to improve patient outcome.

In addition to the advantages offered by including both a targeting moiety and a therapeutic agent, the present disclosure describes methods for constructing and designing nanoparticles. In contrast to previous methods, the methods described herein may be used to produce nanoparticles with consistent pre-determined molecular ratios of the included components, and less variation in nanoparticle size and composition both within batches and between batches. For example, methods described herein may be used to produce nanoparticles with a desired size (e.g., nanoparticles with 80-100 molecules, or 20-40 nm in diameter), a desired targeting molecule valence (e.g., 15-30 targeting molecules, or about 20 targeting molecules), and/or a desired molecular ratio of components.

Figure 13:
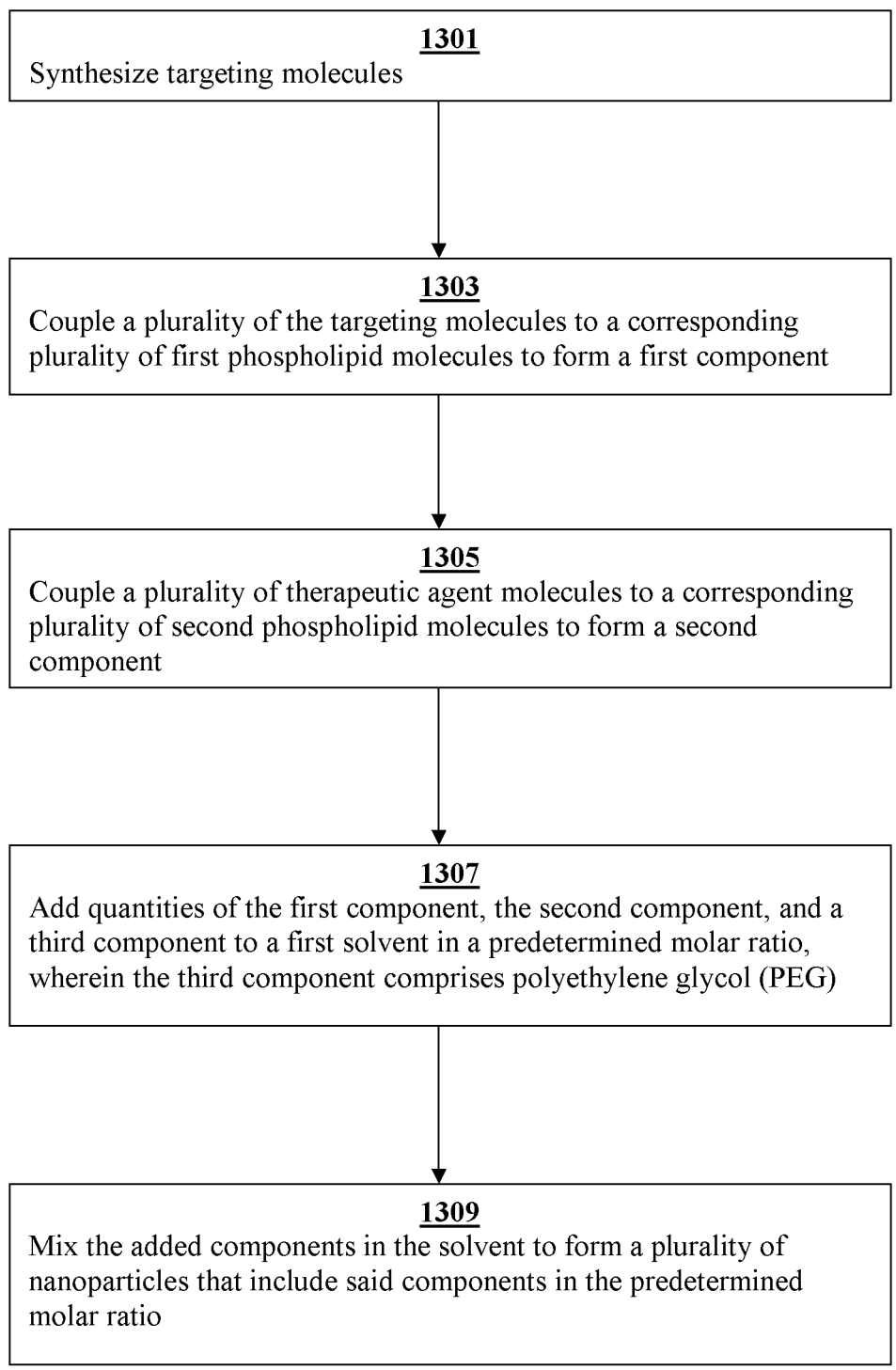
FIG. 13 illustrates a flow diagram of a method for constructing a drug delivery nanoparticle.

FIG. 13 illustrates a flow diagram of a method 1300 for constructing a drug delivery nanoparticle, in accordance with various embodiments.

Optionally, method 1300 may begin at block 1301 with the synthesis of one or more targeting molecules (e.g., targeting molecule 140). A targeting molecule may be, or may include, a peptide, a cyclic peptide, a peptidomimetic, and/or a small molecule. Optionally, the targeting molecule may be an antagonist of a target cell receptor. The targeting molecule may be configured to bind to a target cell, target tissue, or component of extracellular matrix (ECM). In some embodiments, the targeting molecule may be configured to bind to a surface molecule (e.g., an integrin, a cadherin, a selectin, or syndecan) of a target cell. As described in the examples above, the targeting molecule may be configured to trigger endocytosis by the target cell. The targeting molecule may be configured to bind to a surface molecule of a target cell with low affinity. Optionally, the targeting molecule may be configured to reduce or disrupt adhesion of a target cell to another cell or ECM. In a specific example, the targeting molecule may be a VLA-4 antagonist peptide, such as VLA-4-pep (SEQ ID NO: 1).

In some embodiments, method 1300 may further include selecting a targeting molecule. For example, a molecular modeling program may be used to generate a list of possible candidates for targeting a molecule on the target cell, such as a cell surface receptor (e.g., VLA-4). The candidates may be synthesized and screened using binding assays such as titrations, flow cytometry, and/or ELISA assays. One or more of the candidates may be selected for use as targeting molecules based on the binding affinity, the chemistry of conjugation, and/or various molecular properties. In some embodiments, a candidate may be selected for use as a targeting molecule based at least in part on having a binding affinity (to a target cell surface receptor) in the range of 1 nM to 1 µM. Thus, in some embodiments, a targeting molecule may have a binding affinity in the range of 1 nM to 1 µM. Alternatively, the targeting molecules may have a binding affinity in the range of 1 nM to 0.5 µM, 0.1 µM to 0.4p, 0.2 µM to 0.7 µM, or 0.2 µM to 0.3 µM. In embodiments that include the use of the targeting molecule conjugation methodology described in the examples above, candidates may be selected for use as targeting molecule based at least in part on a lack of secondary structure, as the above-described conjugation chemistry will denature the molecule. Optionally, a candidate may be selected for use as a targeting molecule based at least in part on amenability to a solid phase synthetic design.

At block 1303, a plurality of the targeting molecules may be coupled to a corresponding plurality of first lipid molecules to form a first component. In some embodiments, the targeting molecules may be conjugated to the lipid molecules. In some embodiments, the first component may further include a polymer that is conjugated or otherwise coupled to a lipid molecule. The polymer may be a relatively water-soluble polymer, such as polyethylene glycol (PEG).

In one embodiment, the first component may include a targeting molecule coupled to a lipid-PEG block copolymer (e.g., VLA-4-pep coupled to DSPE-PEG2000). Optionally, the targeting molecule may be coupled to a first end of the polymer, and the lipid molecule may be coupled to an opposite second end of the polymer. The targeting molecule may be synthesized on amide resin and reacted with succinic anhydride to generate a carboxylic acid group at the peptide terminus. This carboxylic acid group may then be activated, and DSPE-PEG2000-Amine lipid may be introduced in anhydrous DMF to promote amide coupling before cleaving the peptide-PEG-lipid conjugate from the resin with an acid (e.g., a TFA cocktail).

Optionally, at block 1305, a plurality of therapeutic agent molecules may be coupled to a corresponding plurality of second lipid molecules to form a second component. The second lipid molecules may be lipids of a different species/structure than the first lipid molecules. Alternatively, the second lipid molecules may be lipids of the same species/structure as the first lipid molecules. Some or all of the therapeutic agent molecules may be coupled to the corresponding second lipid molecules by a pH-sensitive bond. For example, some or all of the therapeutic agent molecules may be coupled to the corresponding lipid molecules by an acid-labile bond, such as (but not limited to) a hydrazone (HN—NH) bond. The therapeutic agent molecules can be or include any type of molecules for which delivery to a target cell or tissue is desired. In one example, the therapeutic agent is doxorubicin. In other examples, the therapeutic agent may be another drug (e.g., a chemotherapy drug for treating a cancer), a nucleic acid (e.g., siRNA, DNA, etc.), or some combination thereof. Optionally, some of the molecules of the second lipid may be coupled to corresponding molecules of a first therapeutic agent, and other molecules of the second (or other) lipid may be coupled to corresponding molecules of a second therapeutic agent.

In a specific example, the lipid may be DPPE-GA and the therapeutic agent may be doxorubicin. The DPPE-GA may be coupled to the doxorubicin my mixing the DPPE-GA with hydrazine and diisopropylcarbodiimide, allowing these reagents to react (e.g., for 4 hours at room temperature), removing solvent and excess reactants (e.g., via evaporation under vacuum), re-dissolving the product in chloroform and mixing with doxorubicin in methanol, and allowing these reagents to couple over a period of time (e.g., 3 days).

At block 1307, the first and second components and a third component may be added to a first solvent in a predetermined molar ratio. The predetermined molar ratios of the first, second, and third components may vary among embodiments. The predetermined molar ratio may be a function of the desired molar percentages and/or molecular ratios of the components in the nanoparticles, discussed above. For example, to construct a nanoparticle with a desired molecular ratio of 60:20:10 (third component:first component:second component), the components may be added in a predetermined molar ratio of 6:2:1. The molar percentage of the first component (i.e., targeting component) may be 0-60% (e.g., 0-5%, 0-40%, 1-40%, 10-30%, 15-35%, 20-30%, 20-40%, or 30-40%). The molar percentage of the second component (i.e., therapeutic component) may be 0-25% (e.g., 0-5%, 1-10%, 0-20% 1-20%, 5-15%, 5-20%, or 10-20%). The molar percentage of the third component may be 60-100% (e.g., 60-70%, 60-90%, 70-90%, 75-95%, 80-90%, 80-95%, or 90-100%). In some embodiments, the molar percentage of the third component may be greater than the molar percentage of the first component, which may be greater than the molar percentage of the second component. Alternatively, the molar percentage of the second component may be greater than the molar percentage of the first component.

The ratio of the second component to the first and third components may be selected to result in nanoparticles with a desired number of the targeting molecules for multivalent presentation to the target cell and enhanced binding affinity and/or specificity of ligand-receptor interactions. The third component may be configured to enhance the stability and/or circulation time of a nanoparticle. In some embodiments, the first component may include a polymer that is conjugated or otherwise coupled to a lipid molecule. The polymer may be a relatively water-soluble polymer, such as polyethylene glycol (PEG). In some embodiments, the third component may be a lipid-PEG block copolymer (e.g., DSPE-PEG2000). Optionally, two or more of the first, second, and third components may include the same lipid and/or polymer species. For example, the first component and the third component may include a lipid-PEG block copolymer (e.g., DSPE-PEG2000).

In a particular embodiment, the first component is a peptide-PEG-phospholipid conjugate (e.g., VLA-4-pep/DSPE-PEG2000), the second component is a therapeutic agent conjugated to a phospholipid (e.g., Dox/DPPE-GA), and the third component is a pegylated phospholipid (e.g., DSPE-PEG2000). In this embodiment, the constructed nanoparticles may include 80-100 component molecules, or about 90 component molecules. The predetermined molecular ratio of third component:first component:second component may be 60:20:10. The molar percentages of the third, first, and second components may be about 67%, about 22%, and about 11%, respectively.

At block 1309, the first, second, and third components may be mixed in the first solvent to form a plurality of nanoparticles that include the components in the predetermined molar ratio. The resulting nanoparticles may have diameters in the range of 18-90 nm, 20-50 nm, 20-40 nm, 18-30 nm, or 18-25 nm. Optionally, the first solvent may be removed (e.g., by evaporation) and the nanoparticles may be resuspended in an aqueous solution. In some embodiments, the resulting nanoparticles may be micelles comprising 80-100 molecules, collectively, of the first, second, and third components. In one embodiment, 10-40 of the 80-100 molecules may be molecules of the first component. In a particular embodiment, the nanoparticles may have a diameter of 18-30 nm and a total number of 80-100 molecules, of which 15-25 molecules are molecules of the first component. In still other embodiments, the resulting nanoparticles may be micelles comprising more than 100 molecules or less than 80 molecules.

FIG. 14 illustrates a flow diagram of a method 1400 for designing and using a drug delivery nanoparticle to treat a target cell or tissue, in accordance with various embodiments.

Method 1400 may begin at block 1401 with the selection of a target cell or tissue for treatment with a therapeutic agent. The target cell or tissue may be, for example, a cancerous cell or tissue (e.g., a solid tumor, a blood cell cancer, etc.). The target cell or tissue may have a first surface receptor that is not present on, or is present in fewer numbers or in a different arrangement on, a non-target cell or tissue.

At block 1403, a ligand that binds to the first surface receptor may be selected. In some embodiments, this may be accomplished by screening a variety of potential ligands and selecting one based on binding affinity. In some embodiments, a molecular modeling program may be used to generate a list of possible candidates for targeting a molecule on the target cell, such as a cell surface receptor (e.g., VLA-4). Some candidates may be molecules known in the art for binding to a target cell surface receptor (e.g., known antagonists of a receptor). Optionally, some or all of the candidates may be synthesized. Candidates may be screened using binding assays such as titrations, flow cytometry, and/or ELISA assays. One or more of the candidates may be selected for use as targeting molecules based on the binding affinity, the chemistry of conjugation, and/or various molecular properties. In some embodiments, a candidate may be selected for use as a targeting molecule based at least in part on a binding affinity (to a target cell surface receptor) of 1 nM to 1 µM. In embodiments that include the use of the targeting molecule conjugation methodology described in the examples above, candidates may be selected for use as targeting molecule based at least in part on a lack of secondary structure, as the above-described conjugation chemistry will denature the molecule. Optionally, a candidate may be selected for use as a targeting molecule based at least in part on amenability to a solid phase synthetic design.

Optionally, the targeting molecule may be configured to bind to a surface molecule of a target cell and/or ECM component with low affinity. The targeting molecule may be configured to trigger endocytosis by the target cell upon binding to the surface molecule. Optionally, the targeting molecule may be configured to reduce or disrupt adhesion of a target cell to another cell or ECM. In a specific example, the targeting molecule may be a VLA-4 antagonist peptide, such as VLA-4-pep (SEQ ID NO: 1).

At block 1405, molecules of the selected ligand may be coupled to corresponding molecules of a first lipid molecule to form a first component. In some embodiments, the ligand may be conjugated to the lipid molecules. In some embodiments, the first component may further include a polymer that is conjugated or otherwise coupled to a lipid molecule. The polymer may be a relatively water-soluble polymer, such as polyethylene glycol (PEG). In a specific embodiment, the first component may include a ligand coupled to a lipid-PEG block copolymer (e.g., VLA-4-pep coupled to DSPE-PEG2000). Optionally, the ligand may be coupled to a first end of the polymer, and the lipid molecule may be coupled to an opposite second end of the polymer.

At block 1407, the therapeutic agent may be coupled to a plurality of second lipid molecules to form a second component. Some or all of the therapeutic agent molecules may be coupled to the corresponding second lipid molecules by a pH-sensitive bond, such as (but not limited to) a hydrazone (HN—NH) bond. The therapeutic agent can be or include any type of drug or other agent for which delivery to a target cell or tissue is desired. In one example, the therapeutic agent is doxorubicin. In other examples, the therapeutic agent may be another drug (e.g., a chemotherapy drug for treating a cancer), a nucleic acid (e.g., siRNA, DNA, etc.), or some combination thereof.

At block 1409, nanoparticles may be formed by adding the first and second components and a third component to a first solvent in a predetermined molar ratio. In some embodiments, the mole percentage range for the second component (i.e., therapeutic component) is 0-20%, the mole percentage range for the first component is 0-40%, and the mole percentage range for the third component is 60-100%. The resulting nanoparticles may have diameters and relative ratios of components as described above. In some embodiments, the third component may be a lipid-PEG block copolymer (e.g., DSPE-PEG2000). Optionally, two or more of the first, second, and third components may include the same lipid and/or polymer species. For example, the first component and the third component may include a lipid-PEG block copolymer (e.g., DSPE-PEG2000).

In some embodiments, several groups or batches of nanoparticles may be formed separately, each group having a different molar ratio of the first component to the other components. In other words, each group of nanoparticles may have a different targeting molecule valency. The groups may be tested in vitro to determine an optimal valency or number of targeting molecules per nanoparticle. Nanoparticles with the optimal targeting molecule valency may then be prepared for administration to a patient in need thereof. Optionally, nanoparticles may be tested in vitro by methods known in the art and/or as described above to confirm cell uptake of the nanoparticles.

At block 1411, the nanoparticles may be administered to a patient in need thereof (e.g., a patient having a cell/tissue of the kind targeted for treatment). In some embodiments, the nanoparticles may be administered by intravenous injection. Optionally, the nanoparticles may be administered in a dose that is determined based at least on a recommended or standard dose of the therapeutic agent alone. For example, the nanoparticles may be administered at a dose that is equivalent to (i.e., contains as many molecules of the therapeutic agent as) 10-20%, 20-30%, 30-40%, 40-50%, 50-75%, or 75-100% of the recommended or standard dose of the therapeutic agent alone. Alternatively, the nanoparticles may be administered in a dose that is determined based at least in part on toxicity data. As described above, delivery of a therapeutic agent via nanoparticles may result in reduced toxicity as compared to administration of the therapeutic agent alone. Thus, in some examples, the nanoparticles may be administered in a dose that is equivalent to 100-200% or more of the recommended or standard dose of the therapeutic agent alone. In some examples, the nanoparticles may be administered in a dose that is equivalent to 150% or more of the recommended or standard dose of the therapeutic agent alone.

At block 1413, the effect of the nanoparticles on the target cell or tissue may be measured. In some embodiments, the effect of the nanoparticles may be measured by measuring the size of a tumor before administration of the nanoparticles, measuring the size of the tumor at one or more time points after the administration of the nanoparticles, and comparing the measurements. In other embodiments, the effect of the nanoparticles may be measured by other known methods.

Thus, embodiments of the present disclosure provide nanoparticles having a hydrophobic interior portion surrounded by an outer portion, a therapeutic agent coupled to, and disposed at least partially within, the outer portion, and a targeting agent coupled to, and disposed at least partially within, the outer portion. The outer portion may comprise a water-soluble polymer. The nanoparticle may be a micellar nanoparticle. The water-soluble polymer may be coupled to a first lipid, the therapeutic agent may be coupled to a second lipid, and the targeting agent may be coupled to a third lipid. The first, second, and third lipids may be disposed within the interior portion of the nanoparticle. The water-soluble polymer may be polyethylene glycol (PEG). The therapeutic agent may be an antibiotic or an anti-cancer drug, such as doxorubicin. The targeting agent may comprise a peptide (e.g., VLA-4-pep; SEQ ID NO: 1). The targeting agent may be configured to bind to a receptor of a target cell. The nanoparticle may have a size of about 20 nm, and may include 10 to 20 or 20 to 40 molecules of the targeting agent. In some examples, the water-soluble polymer comprises polyethylene glycol (PEG), and the therapeutic agent is coupled to the second lipid via a pH-sensitive bond. In a specific example, the targeting agent is configured to bind to a VLA-4 receptor of a target cell, the therapeutic agent comprises doxorubicin, and the pH-labile bond is configured to hydrolyze at the pH of an endocytic vesicle of the target cell.

Other embodiments of the present disclosure provide methods of delivering a therapeutic agent to a cell or tissue of interest in an individual. One method may comprise administering to the individual a nanoparticle having a hydrophobic interior portion surrounded by an outer portion, a therapeutic agent coupled to, and disposed at least partially within, the outer portion; and a targeting agent coupled to, and disposed at least partially within, the outer portion. The targeting agent of the nanoparticle may enhance accumulation of said therapeutic agent in the cell or tissue of interest. The targeting agent may bind to a receptor of the cell or tissue of interest, and the targeting agent may enhance receptor-mediated endocytosis of the nanoparticle by the cell or tissue of interest. The cell or tissue of interest may be a cancerous cell or tissue, such as a multiple myeloma cell. In some examples, the targeting agent is VLA-4-pep (SEQ ID NO: 1) and the therapeutic agent is doxorubicin.

Other embodiments of the present disclosure provide a pharmaceutical composition comprising a nanoparticle and a pharmacologically acceptable excipient. The nanoparticle may have a hydrophobic interior portion surrounded by an outer portion, a therapeutic agent coupled to, and disposed at least partially within, the outer portion, and a targeting agent coupled to, and disposed at least partially within, the outer portion.

Other embodiments of the present disclosure provide nanoparticles for the preparation of a pharmaceutical composition for the treatment of a cancer. The nanoparticles may comprise a hydrophobic interior portion surrounded by an outer portion, a therapeutic agent coupled to, and disposed at least partially within, the outer portion, and a targeting agent coupled to, and disposed at least partially within, the outer portion.

Other embodiments of the present disclosure provide methods of constructing a nanoparticle-based drug delivery system. One method may comprise adding quantities of a first component, a second component, and a third component to a solvent in a predetermined molar ratio, wherein the first component comprises a targeting molecule coupled to a first lipid molecule, the second component comprises a therapeutic agent coupled to a second lipid molecule, and the third component comprises polyethylene glycol (PEG), and mixing said components in the solvent to form a plurality of nanoparticles that include said components in the predetermined molar ratio. The nanoparticles may have a hydrophobic interior portion surrounded by an outer portion. The first and second lipid molecules may be disposed in the interior portion, and the PEG, the targeting molecule, and the therapeutic agent may be disposed in the outer portion. The method may further include coupling the targeting molecule to the first lipid molecule to form the first component prior to said mixing. The method may also include coupling the therapeutic agent to the second lipid molecule to form the second component prior to said mixing. In some embodiments, the method may further include synthesizing the targeting molecule on a solid support and cleaving the targeting molecule from the solid support after coupling the targeting molecule to the first lipid molecule.

The nanoparticles may be micelles with a diameter of about 20 nm. The targeting molecule may comprise a peptide, and coupling the targeting molecule to the first lipid molecule may include conjugating the peptide to the lipid molecule. The therapeutic agent may be coupled to the second lipid molecule by a pH-sensitive bond. In some embodiments, the therapeutic agent comprises an antineoplastic drug. The targeting molecule may be configured to bind to a receptor of a target cell. In some examples, the targeting molecule is VLA-4-pep (SEQ ID NO: 1) and the therapeutic agent is doxorubicin. The third component may include a third lipid molecule coupled to the PEG. Optionally, the first lipid molecule and/or the third lipid molecule may comprise DSPE. The predetermined molecular ratio of the first component to the second and third components in the nanoparticles may be about 20:70.

Other embodiments of the present disclosure provide methods for designing a drug delivery system to treat a disease or other medical condition. One method may comprise selecting a target cell or tissue for treatment with a first therapeutic agent, wherein the surface of the selected target cell or tissue includes a first surface receptor, selecting a ligand that binds to the first surface receptor, and adding quantities of a first component, a second component, and a third component to a first solvent in a predetermined molar ratio to form nanoparticles. The first component may include the ligand coupled to a first lipid. The second component may include the therapeutic agent coupled to a second lipid. The third component may comprise polyethylene glycol (PEG). In some embodiments, the method may further comprise coupling the ligand to the first lipid to form the first component. In other embodiments, the method may further comprise coupling the first therapeutic agent to the second lipid to form the second component. The nanoparticle may be a micelle with a lipid core surrounded by an outer layer. The targeting agent, the therapeutic agent, and the PEG may be disposed in the outer layer. Optionally, the method may further comprise measuring an effect of the nanoparticles on the target cell or tissue.

Other embodiments of the present disclosure provide methods of treating a disease or other medical condition. One method may include administering to a patient in need thereof a nanoparticle having a hydrophobic interior portion surrounded by an outer portion, a therapeutic agent coupled to, and disposed at least partially within, the outer portion; and a targeting agent coupled to, and disposed at least partially within, the outer portion. The disease may be a cancer and the therapeutic agent may be a chemotherapeutic agent. The targeting agent may be a ligand for a cell surface receptor expressed by a cancerous cell or tissue. In a particular embodiment, the disease is multiple myeloma, the therapeutic agent is doxorubicin, and the targeting agent is VLA-4-pep (SEQ ID NO: 1). The method may further comprise measuring an effect of the nanoparticles on the target cell or tissue.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A micellar nanoparticle comprising:
   a hydrophobic interior portion surrounded by an outer portion, the outer portion comprising a water-soluble polymer;
   a therapeutic agent coupled to, and disposed at least partially within, the outer portion; and
   a targeting agent coupled to, and disposed at least partially within, the outer portion, wherein the targeting agent is a low-affinity, high-specificity peptide ligand of a conjugate of the formula:

[chemical structure showing VLA₄-pep linked via amide, PEG (n=45), phosphate, glycerol and two C16 acyl chains]

wherein VLA₄-pep is a peptide of SEQ ID NO: 1.

2. The nanoparticle of claim 1, wherein the water-soluble polymer is coupled to a first lipid, the therapeutic agent is coupled to a second lipid, and the targeting agent is coupled to a third lipid, and the first, second, and third lipids are disposed within the interior portion of the nanoparticle.

3. The nanoparticle of claim 2, wherein the water-soluble polymer is polyethylene glycol (PEG).

4. The nanoparticle of claim 1, wherein the therapeutic agent comprises an antibiotic.

5. The nanoparticle of claim 4, wherein the therapeutic agent is doxorubicin.

6. The nanoparticle of claim 1, wherein the nanoparticle further comprises one or more targeting agents comprising the peptide sequence CFLDFP (SEQ ID NO: 2), (X)CDPC (SEQ ID NO: 3), XC(Z)PC (SEQ ID NO: 4), XCA(Z)C (SEQ ID NO: 5), (X)CSPC (SEQ ID NO: 6), YC(X)C (SEQ ID NO: 7), or RC(X)PC (SEQ ID NO: 8) where X and Z are variable amino acids.

7. The nanoparticle of claim 6, wherein the targeting agent comprises the peptide sequence CFLDFP (SEQ ID NO: 2).

8. The nanoparticle of claim 1, wherein the nanoparticle has a size of about 20 nm and includes 10 to 40 molecules of said targeting agent.

9. The nanoparticle of claim 2, wherein the water-soluble polymer comprises polyethylene glycol (PEG), and the therapeutic agent is coupled to the second lipid via a pH-sensitive bond.

10. The nanoparticle of claim 9, wherein the targeting agent is configured to bind to a VLA-4 receptor of a target cell, the therapeutic agent comprises doxorubicin, and the pH-sensitive bond is configured to hydrolyze at the pH of an endocytic vesicle of the target cell.

11. A method of delivering a therapeutic agent to a cell or tissue of interest in an individual, comprising administering the nanoparticle of claim 1 to a patient in need thereof, wherein the targeting agent of said nanoparticle enhances accumulation of said therapeutic agent in the cell or tissue of interest.

12. The method of claim 11, wherein the targeting agent binds to a receptor of the cell or tissue of interest, and the targeting agent enhances receptor-mediated endocytosis of the nanoparticle by the cell or tissue of interest.

13. The method of claim 11, wherein the cell or tissue of interest is a cancerous cell or tissue.

14. The method of claim 13, wherein the cell or tissue of interest is a multiple myeloma cell.

15. The method of claim 13, wherein the therapeutic agent is doxorubicin.

16. A pharmaceutical composition comprising the nanoparticle of claim 1 and a pharmacologically acceptable excipient.

17. A micellar nanoparticle comprising:
   a hydrophobic interior portion surrounded by an outer portion, the outer portion comprising a water-soluble polymer conjugated to a phospholipid;
   a therapeutic agent coupled to, and disposed at least partially within, the outer portion, wherein the therapeutic agent coupled to the outer portion is a phospholipid conjugate of the formula:

[chemical structure showing phospholipid with two C14 acyl chains, phosphate, ethanolamine linker, succinyl amide, and doxorubicin moiety]

and a targeting agent coupled to, and disposed at least partially within, the outer portion, wherein the targeting agent is a low-affinity, high-specificity peptide ligand of the formula:

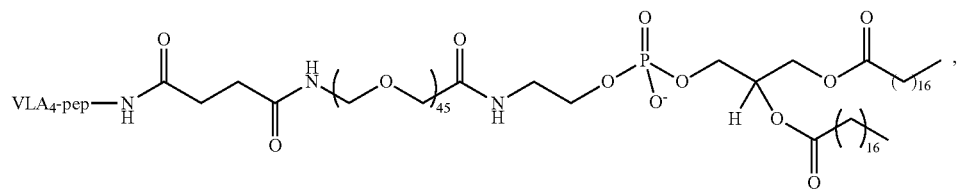
10
wherein VLA₄-pep is a peptide of SEQ ID NO: 1.
18. A pharmaceutical composition comprising the nanoparticle of claim 17 and a pharmacologically acceptable excipient.
* * * * *

SEQUENCE LISTING

<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (2)..(5)

<400> SEQUENCE: 1

Tyr Cys Asp Pro Cys
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic construct

<400> SEQUENCE: 2

Cys Phe Leu Asp Phe Pro
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Xaa is any amino acid
<220> FEATURE:
<221> NAME/KEY: misc_feature
<222> LOCATION: (1)..(1)
<223> OTHER INFORMATION: Xaa is any amino acid

<400> SEQUENCE: 3

Xaa Cys Asp Pro Cys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is any amino acid
<220> FEATURE:
<221> NAME/KEY: misc_feature
<222> LOCATION: (3)..(3)
<223> OTHER INFORMATION: Xaa is any amino acid

<400> SEQUENCE: 4

Xaa Cys Xaa Pro Cys
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic construct

```
<220> FEATURE:
<221> NAME/KEY: misc_feature
<222> LOCATION: (1)..(1)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is any amino acid

<400> SEQUENCE: 5

Xaa Cys Ala Xaa Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is any amino acid

<400> SEQUENCE: 6

Xaa Cys Ser Pro Cys
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa is any amino acid

<400> SEQUENCE: 7

Tyr Cys Xaa Cys
1

<210> SEQ ID NO 8
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa is any amino acid

<400> SEQUENCE: 8

Arg Cys Xaa Pro Cys
1               5
```